United States Patent
Garrison et al.

(10) Patent No.: US 12,396,835 B1
(45) Date of Patent: Aug. 26, 2025

(54) INTERVENTIONAL SYSTEMS AND ASSOCIATED DEVICES AND METHODS

(71) Applicant: Intervene, Inc., South San Francisco, CA (US)

(72) Inventors: Michi E. Garrison, Half Moon Bay, CA (US); Kent D. Dell, Lincoln, CA (US); Jeffrey M. Elkins, Woodside, CA (US); Daniel T. Lagoe, Pacifica, CA (US); Herbert M. Mendoza, South San Francisco, CA (US)

(73) Assignee: Intervene, Inc.

( * ) Notice: Subject to any disclaimer, the term of this patent is extended or adjusted under 35 U.S.C. 154(b) by 0 days.

(21) Appl. No.: 19/200,521

(22) Filed: May 6, 2025

Related U.S. Application Data

(63) Continuation of application No. 18/916,474, filed on Oct. 15, 2024, now Pat. No. 12,290,278, which is a
(Continued)

(51) Int. Cl.
*A61F 2/01* (2006.01)
*A61B 17/3207* (2006.01)

(52) U.S. Cl.
CPC ...... *A61F 2/013* (2013.01); *A61B 17/320725* (2013.01); *A61F 2/0105* (2020.05); *A61F 2002/016* (2013.01)

(58) Field of Classification Search
CPC .............. A61B 17/221; A61B 17/3207; A61B 2017/320775; A61B 17/32037; A61B 17/22031; A61B 2017/22034; A61B 17/32075; A61B 2017/00778; A61B 2017/320716; A61B 2017/320008;
(Continued)

(56) References Cited

U.S. PATENT DOCUMENTS 5,071,424 A * 12/1991 Reger .............. A61B 17/32075
606/159
5,224,945 A 7/1993 Pannek, Jr.
(Continued)

FOREIGN PATENT DOCUMENTS

EP 2278926 B1 4/2017
WO 2022192897 A1 9/2022

OTHER PUBLICATIONS

Communication Pursuant to Rule 164(2)(b) and Article 94(3) issued in European Patent Application No. 22713837.7, issued on Jul. 1, 2025, 10 pages.
(Continued)

*Primary Examiner* — Katherine Shi
(74) *Attorney, Agent, or Firm* — Dorsey & Whitney LLP

(57) ABSTRACT

According to some embodiments, the present technology includes device for removing obstructive material from a blood vessel lumen. For example, the device can comprise an elongated member, a cutting portion carried by a distal region of the elongated member, and a capture portion carried by the distal region of the elongated member. The cutting portion can comprise a blade configured to separate at least a portion of the obstructive material from the blood vessel wall, and the capture portion can comprise a mesh structure configured to enmesh and/or capture at least a portion of the obstructive material.

4 Claims, 25 Drawing Sheets

Related U.S. Application Data continuation of application No. 17/654,398, filed on Mar. 10, 2022.

(60) Provisional application No. 63/200,495, filed on Mar. 10, 2021.

(58) Field of Classification Search
CPC .. A61B 17/32002; A61B 2017/320032; A61B 2017/22094; A61B 17/22012; A61B 17/320758; A61B 17/32; A61B 17/3205; A61B 17/320725; A61B 2017/320733; A61B 2017/320741; A61B 2017/320766; A61B 2017/00685; A61B 17/320016; A61B 2017/320024; A61B 2017/320028
See application file for complete search history.

(56) References Cited

U.S. PATENT DOCUMENTS

| | | | |
|---|---|---|---|
| 5,827,324 A | 10/1998 | Cassell et al. | |
| 6,066,158 A | 5/2000 | Engelson et al. | |
| 6,454,775 B1 | 9/2002 | Demarais et al. | |
| 6,652,548 B2 | 11/2003 | Evans et al. | |
| 7,323,001 B2 | 1/2008 | Clubb et al. | |
| 8,328,810 B2 | 12/2012 | Patel et al. | |
| 8,419,748 B2 | 4/2013 | Valaie | |
| 9,308,016 B2 | 4/2016 | Escudero et al. | |
| 9,700,332 B2 | 7/2017 | Marchand et al. | |
| 10,231,751 B2 | 3/2019 | Sos | |
| 10,251,667 B2 | 4/2019 | Cohen et al. | |
| 10,779,852 B2 | 9/2020 | Bruzzi et al. | |
| 11,259,820 B2 | 3/2022 | Walzman | |
| 11,344,327 B2 | 5/2022 | Fernandez et al. | |
| 11,877,752 B2 | 1/2024 | Walzman | |
| 12,290,278 B2 | 5/2025 | Garrison et al. | |
| 2002/0010487 A1 | 1/2002 | Evans et al. | |
| 2003/0055444 A1* | 3/2003 | Evans | A61B 17/320725 606/159 |
| 2004/0082962 A1* | 4/2004 | Demarais | A61B 17/320725 606/128 |
| 2004/0219028 A1 | 11/2004 | Demarais et al. | |
| 2014/0052103 A1 | 2/2014 | Cully et al. | |
| 2015/0157443 A1 | 6/2015 | Hauser et al. | |
| 2018/0000509 A1 | 1/2018 | Wilson et al. | |
| 2018/0193043 A1 | 7/2018 | Marchand et al. | |
| 2020/0146709 A1 | 5/2020 | Vetter et al. | |
| 2021/0307767 A1 | 10/2021 | Gifford et al. | |
| 2021/0315597 A1 | 10/2021 | Buck et al. | |
| 2021/0393275 A1 | 12/2021 | Whelan | |
| 2022/0249121 A1* | 8/2022 | Wang | A61B 17/320758 |
| 2022/0287817 A1 | 9/2022 | Garrison et al. | |

OTHER PUBLICATIONS

International Search Report and Written Opinion mailed Jul. 5, 2022; International Application No. PCT/ US2022/071076; 18 pages.

* cited by examiner

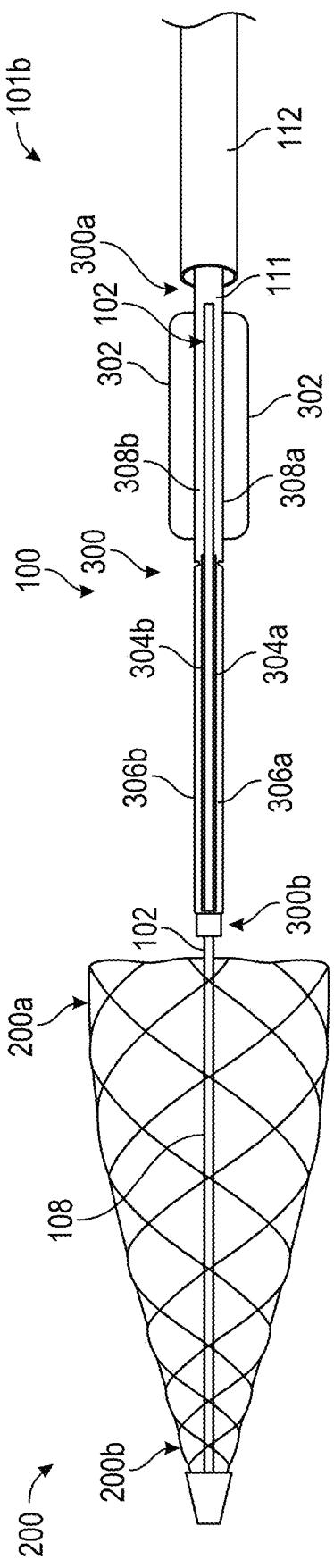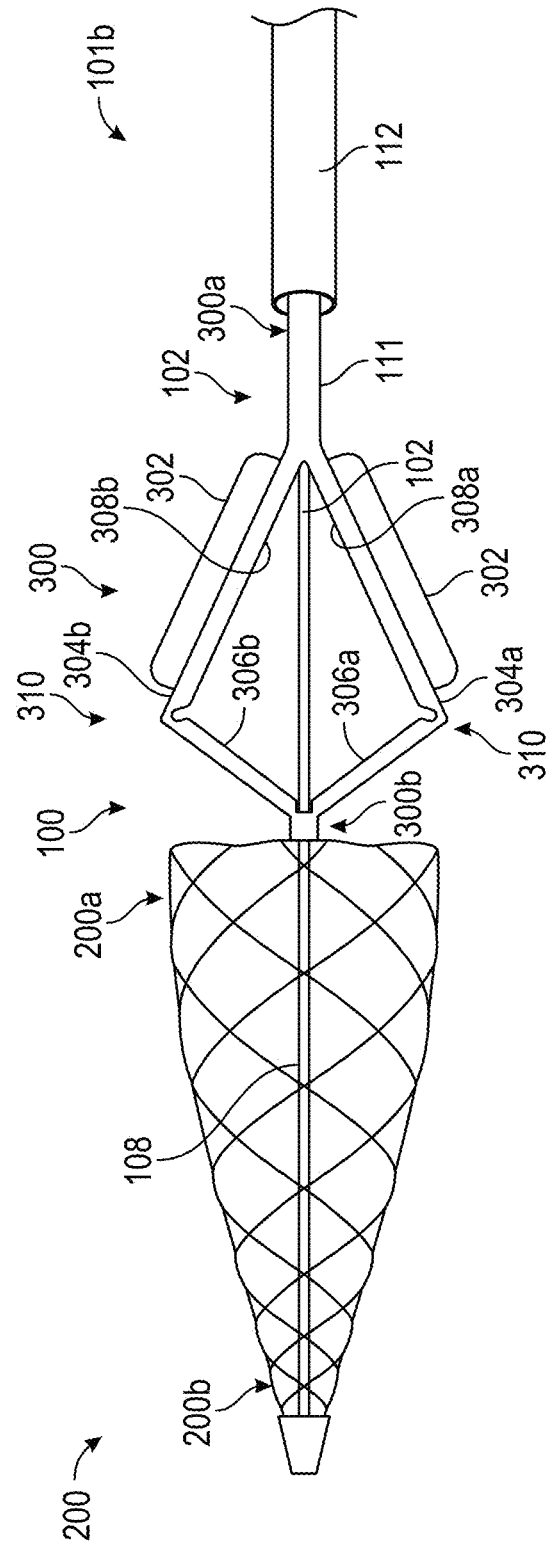
FIG. 3A
FIG. 3B

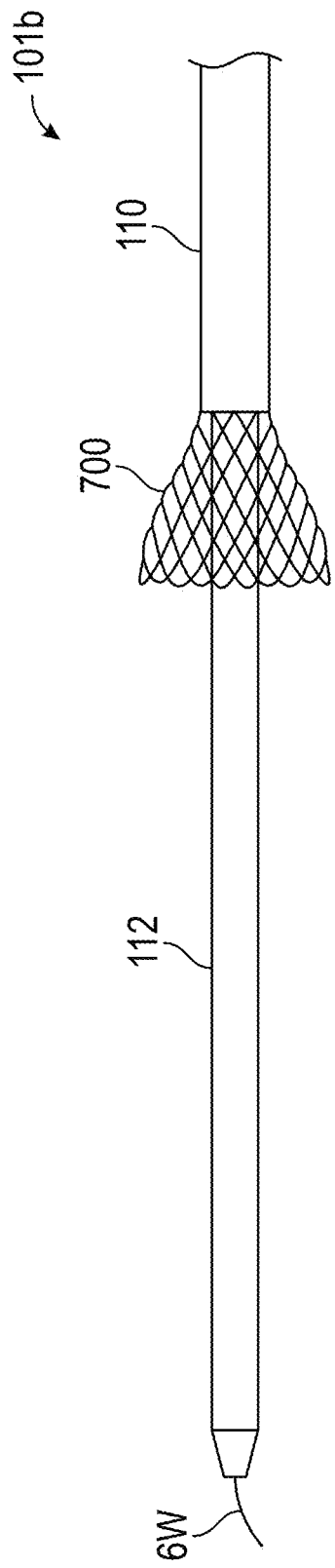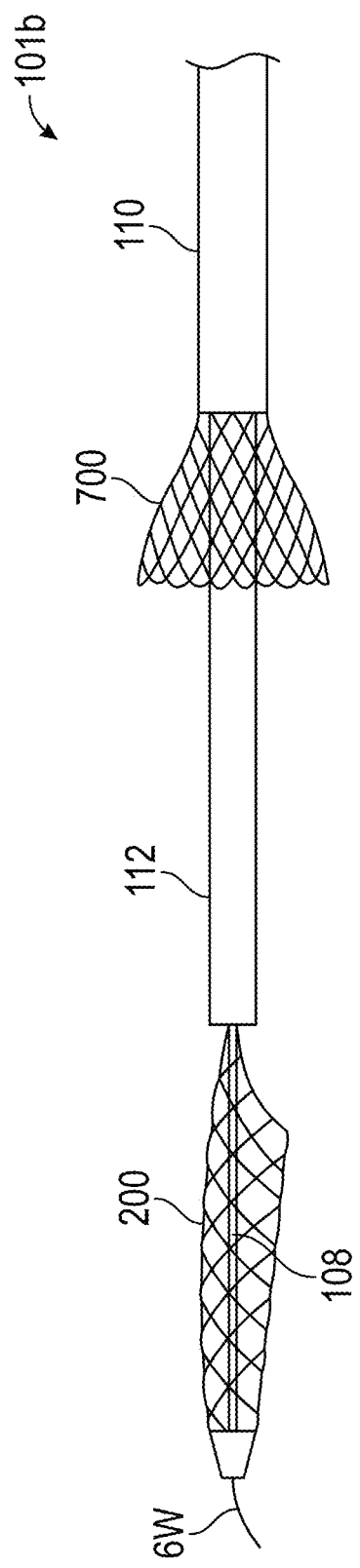

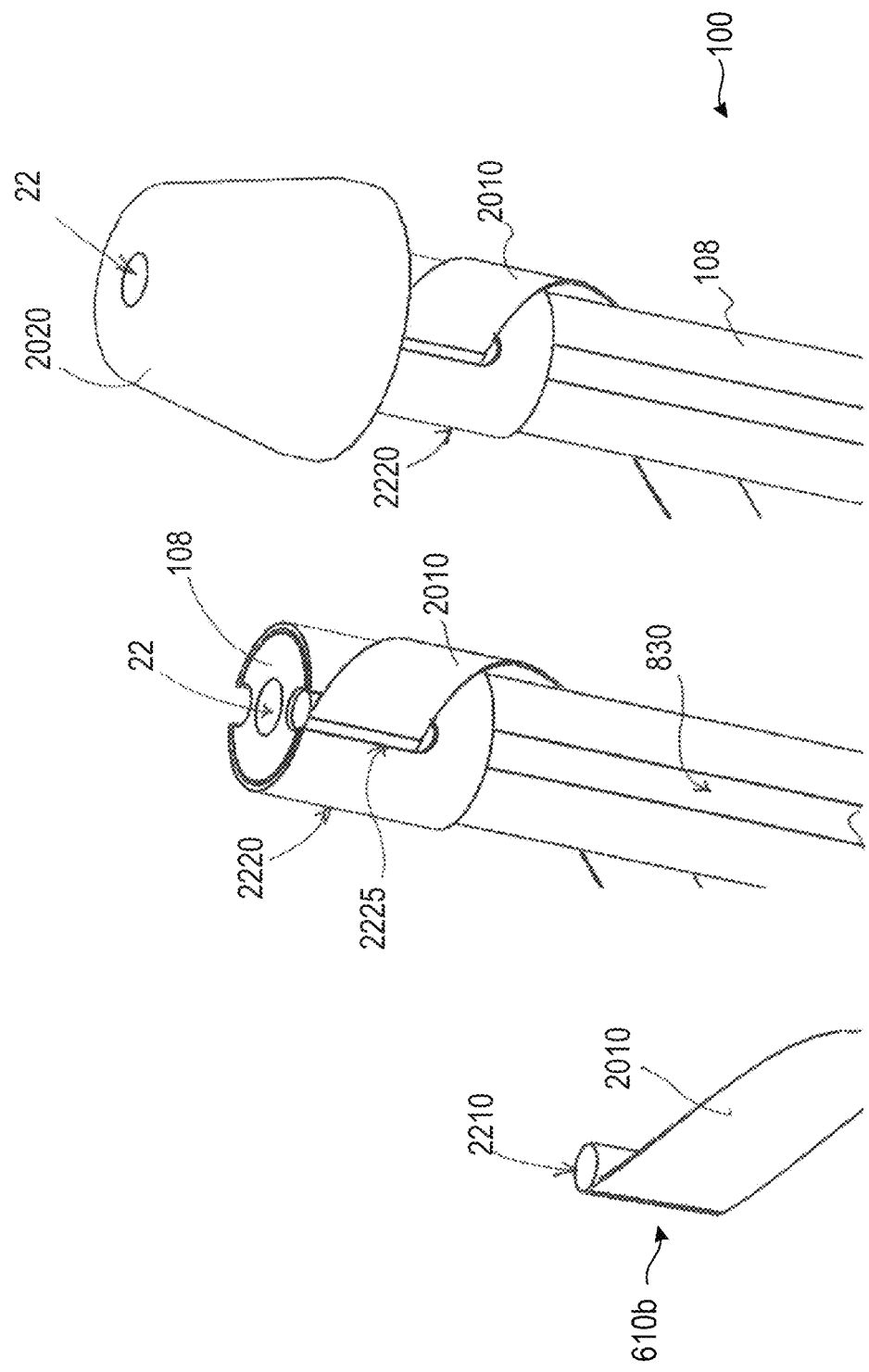

INTERVENTIONAL SYSTEMS AND ASSOCIATED DEVICES AND METHODS

CROSS-REFERENCE TO RELATED APPLICATION(S)

This application is a continuation of U.S. patent application Ser. No. 18/916,474, filed Oct. 15, 2024, issued as U.S. Pat. No. 12,290,278 on May 6, 2025, which in turn is a continuation of U.S. patent application Ser. No. 17/654,398, filed Mar. 10, 2022, which claims the benefit of priority to U.S. Provisional Application No. 63/200,495, filed Mar. 10, 2021, each of which is incorporated by reference herein by reference in its entirety.

TECHNICAL FIELD

The present technology relates generally to interventional systems and associated devices and methods.

BACKGROUND

Deep vein thrombosis (DVT) is a condition comprising a blood clot in a deep vein, usually a leg vein though they can also occur in arm veins. Symptoms include pain, swelling, tenderness, and/or discoloration in the affected limb. If untreated, it can lead to worsening of symptoms and complications such as post-thrombotic syndrome with symptoms of chronic pain, swelling, and skin discoloration, or pulmonary embolism (PE), a very serious and life-threatening condition. Pharmacologic treatments include blood-thinning medications or thrombolytic drugs. More recently, percutaneous catheters have been developed for the more rapid removal of clot to remove the blockage and prevent PE. These include catheters which can deliver thrombolytic agents to the site of the clot, in some cases in combination with aspiration and/or the disruption of the clot into smaller pieces. Other catheters mechanically capture and remove clot without thrombolytic agents, thereby reducing the bleeding risk incurred by these drugs. An early example of this is the Fogarty Balloon Thrombectomy catheter. More recent examples include the ClotTriever® (Inari Medical, Irvine, CA) and the ReVene® Thrombectomy Catheter (Vetex Medical, Galway, Ireland).

Unfortunately, many of these therapies have limited success for partial or full blockages caused by chronic thrombus (i.e., a thrombus over one or two months old). As the clot remains in the limb over a period of months, the initial thrombus transforms into a fibrin and/or collagen structure which is tougher and more firmly adhered to the wall. Chronic thrombus may take the form of fibrous trabeculae or membranes stretching into and across the vein lumen (also known as venous synechiae). Further, the thrombus becomes more firmly attached to the wall. Catheter-based thrombolysis or thrombectomy devices have a lower success rate in removing these blockages. Venous synechiae may also prevent optimal treatment of venous obstruction by balloon angioplasty or stenting, as the fibrous structures prevent permanent stretching of the vessel wall. There is a need for an improved endovascular thrombectomy device which is able to successfully remove chronic thrombus.

SUMMARY

The subject technology is illustrated, for example, according to various aspects described below, including with reference to FIGS. 1-28B. Various examples of aspects of the subject technology are described as numbered clauses (1, 2, 3, etc.) for convenience. These are provided as examples and do not limit the subject technology.

1. A device for modifying and/or removing obstructive material from a lumen of a blood vessel, the device comprising:
   an elongated member having a proximal portion and a distal portion configured to be intravascularly positioned at a treatment site in a blood vessel adjacent obstructive material;
   a cutting portion disposed at the distal portion of the elongated member, the cutting portion including a cutting element, wherein the cutting portion has a collapsed, low-profile state for delivery to the treatment site and a deployed state for cutting obstructive material at the treatment site, and wherein the cutting element extends radially away from the longitudinal axis of the elongated member in the deployed state; and
   a capturing portion disposed at the distal portion of the elongated member, wherein the capturing portion is configured to collect obstructive material that has been dislodged by the cutting portion.
2. The device of Clause 1, wherein the capturing portion is positioned distal of the cutting portion along the elongated member.
3. The device of Clause 1 or Clause 2, wherein the capturing portion is self-expandable.
4. The device of any one of Clauses 1 to 3, wherein the elongated member comprises a first elongated member and a second elongated member, and wherein the cutting portion is disposed at a distal portion of the first elongated member and the capturing portion is disposed at a distal portion of the second elongated member.
5. The device of Clause 4, wherein the first and second elongated members are configured to rotate and/or translate relative to one another.
6. The device of Clause 4 or Clause 5, wherein the second elongated member is configured to be slidably disposed within a lumen of the first elongated member.
7. The device of Clause 4 or Clause 5, wherein the first elongated member is configured to be slidably disposed within a lumen of the second elongated member.
8. The device of any one of Clauses 1 to 7, wherein the cutting portion comprises a blade disposed along a portion of the cutting element.
9. The device of Clause 8, wherein the blade is disposed along only a proximally facing surface of the cutting element.
10. The device of any one of Clauses 1 to 9, wherein a cutting edge of the cutting element is substantially linear.
11. The device of any one of Clauses 1 to 9, wherein the cutting element wraps around a longitudinal axis of the shaft.
12. The device of any one of Clauses 1 to 9, wherein the cutting element is a first cutting element and the device further comprises a second cutting element that is configured to extend radially away from the longitudinal axis of the elongated shaft in the deployed state.
13. The device of Clause 12, wherein an angle between the first and second cutting elements in the deployed state is less than 180 degrees.
14. The device of Clause 12, wherein an angle between the first and second cutting elements in the deployed state is from about 135 degrees to about 180 degrees.

15. The device of any one of Clauses 1 to 14, wherein the capturing portion and the cutting portion are independently deployable.

16. The device of any one of Clauses 1 to 15, wherein the capturing portion comprises has a closed distal end portion and an open proximal end portion.

17. The device of any one of Clauses 1 to 16, wherein the capturing portion comprises a mesh.

18. The device of any one of Clauses 1 to 17, wherein the capturing portion has a first region comprising a braid and a second region comprises a stent.

19. The device of any one of Clauses 1 to 18, wherein, in a deployed state, the cutting element has a proximally facing portion and a distally facing portion, and wherein a sharpened edge of the cutting element is disposed along only the proximally facing portion.

20. The device of any one of Clauses 1 to 18, wherein, in a deployed state, the cutting element has a proximally facing portion and a distally facing portion, and wherein a sharpened edge of the cutting element is disposed along only the distally facing portion.

21. A system for modifying and/or removing obstructive material from a lumen of a blood vessel, the system comprising:
    a first elongated member having a proximal portion and a distal portion configured to be intravascularly positioned at a treatment site in a blood vessel adjacent obstructive material;
    a second elongated member having a proximal portion and a distal portion configured to be intravascularly positioned at the treatment site;
    a cutting portion disposed at the distal portion of the first elongated member, the cutting portion including a cutting element, wherein the cutting portion has a collapsed, low-profile state for delivery to the treatment site and a deployed state for cutting obstructive material at the treatment site, and wherein the cutting element extends radially away from the longitudinal axis of the first elongated member in the deployed state; and
    a capturing portion disposed at the distal portion of the second elongated member, wherein the capturing portion is configured to collect obstructive material that has been dislodged by the cutting portion.

22. The system of Clause 21, wherein the second elongated member is slidably disposed within a lumen of the first elongated member.

23. The system of Clause 21, wherein the first elongated member is slidably disposed within a lumen of the second elongated member.

24. The system of any one of Clauses 21 to 23, wherein a distal region of the cutting portion is axially fixed to the distal portion of the second elongated member and a proximal region of the cutting portion is configured to move axially along the second elongated member.

25. The system of any one of Clauses 21 to 14, wherein, in a deployed state, the cutting element has a proximally facing portion and a distally facing portion, and wherein a sharpened edge of the cutting element is disposed along only the proximally facing portion.

26. The system of any one of Clauses 21 to 24, wherein, in a deployed state, the cutting element has a proximally facing portion and a distally facing portion, and wherein a sharpened edge of the cutting element is disposed along only the distally facing portion.

27. The system of any one of Clauses 21 to 26, further comprising an introducer sheath, and wherein the first and second elongated members are configured to be slidably disposed in a lumen of the introducer sheath.

28. A device for modifying and/or removing obstructive material from a lumen of a blood vessel, the system comprising:
    a first elongated member having a proximal portion and a distal portion configured to be intravascularly positioned at a treatment site in a blood vessel adjacent obstructive material, wherein the first elongated member defines a lumen extending therethrough;
    a second elongated member having a proximal portion and a distal portion configured to be intravascularly positioned at the treatment site, wherein the second elongated member is configured to be rotatably disposed within the lumen of the first elongated member;
    a cutting element configured to cut obstructive material at the treatment site, the cutting element having a proximal end region at the distal portion of the first elongated member and a distal end region at the distal portion of the second elongated member, wherein rotation of the second elongated member relative to the first elongated member, or vice versa, causes the cutting element to expand away from a longitudinal axis of the second elongated member.

29. The device of Clause 28, wherein the cutting element wraps at least partially around the longitudinal axis of the second elongated member as it extends between the first elongated member and the second elongated member.

30. The device of Clause 28 or Clause 29, wherein the cutting element is a ribbon.

31. The device of any one of Clauses 28 to 30, wherein the cutting element has longitudinally extending edges, and wherein one or both longitudinally extending edges are sharpened.

32. The device of any one of Clauses 28 to 30, wherein the cutting element has a proximally facing longitudinal edge and a distally facing longitudinal edge, and wherein only one of the proximally facing or distally facing longitudinal edge is sharpened.

33. The device of any one of Clauses 28 to 32, wherein the cutting element is a first cutting element and the device comprises a second cutting element.

34. The device of Clause 33, wherein the second cutting element is positioned radially inwardly of the first cutting element.

35. The device of Clause 33, wherein the second cutting element is positioned radially outwardly of the first cutting element.

36. The device of any one of Clauses 33 to 35, wherein the second cutting element is substantially linear.

37. The device of any one of Clauses 33 to 35, wherein the second cutting element wraps at least partially around the longitudinal axis of the second elongated member.

38. The device of any one of Clauses 33 to 37, further comprising a third elongated member positioned between the first and second elongated members, and wherein the second cutting element is at a distal portion of the third elongated member.

BRIEF DESCRIPTION OF THE DRAWINGS

Many aspects of the present disclosure can be better understood with reference to the following drawings. The components in the drawings are not necessarily to scale.

Instead, emphasis is placed on illustrating clearly the principles of the present disclosure.

FIGS. 3A and 3B are top views of a treatment assembly configured in accordance with several embodiments of the present technology, shown in a collapsed state and an expanded state, respectively.

FIGS. 12A-12C are side views of a treatment system having a treatment device and an introducer sheath with a proximal funnel configured in accordance with several embodiments of the present technology.

FIGS. 22A, 22B, and 22C are perspective views of a treatment assembly configured in accordance with several embodiments of the present technology, shown with various components removed for ease of explanation.

FIG. 27A shows the cutting portion in a collapsed state. FIG. 27B shows the cutting portion in an expanded state.

FIG. 28A shows the cutting portion in a collapsed state. FIG. 28B shows the cutting portion in an expanded state.

DETAILED DESCRIPTION

Figure 1:
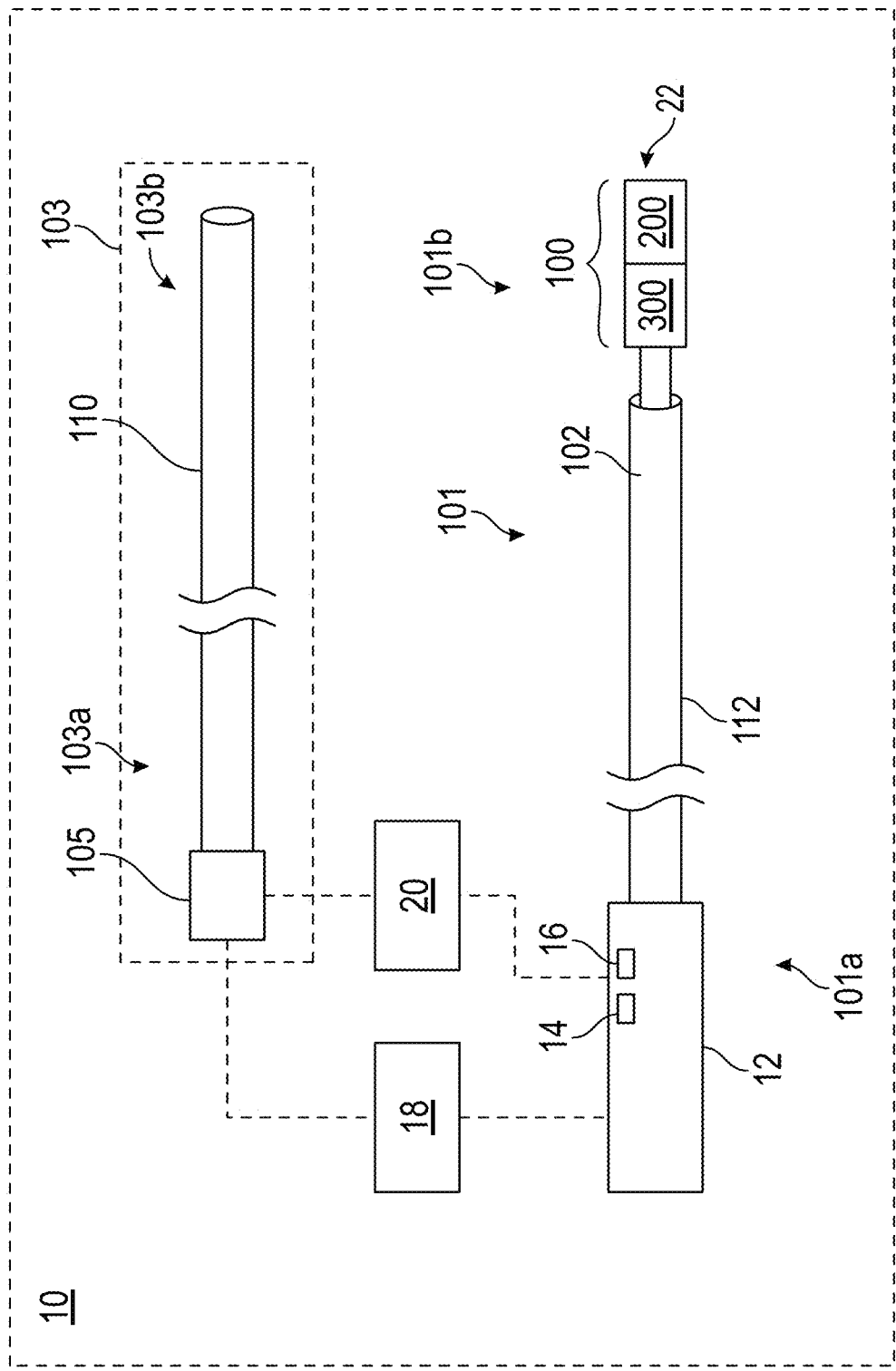
FIG. 1 schematically depicts a treatment system configured in accordance with several embodiments of the present technology.

FIG. 1 schematically depicts a treatment system 10 (also referred to herein as "the system 10") configured in accordance with the present technology. The treatment system 10 is configured to access a body lumen (such as a vein or artery) and modify, capture, and/or remove obstructive material from the body lumen. As used herein, "obstruction" or "obstructive material" can comprise, for example, clot material, atherosclerotic plaque, and/or other flow-obstructing structures, including those derivative of clot material, such as fibrotic clot material, venous synechiae, fibrinous structures, collagenous structures, fibrous trabeculae, and/or others. As shown in FIG. 1, the system 10 may comprise a treatment device 101 (or "device 101") having a proximal portion 101a configured to be positioned extracorporeally during the procedure, a distal portion 101b configured to be positioned at a treatment site within a blood vessel, and one or more elongated members 102 extending between the proximal portion 101a and the distal portion 101b. The treatment device 101 can also include a handle 12 and a sleeve 112 extending distally from the handle 12. The elongated member 102 can be configured to be slidably disposed within a lumen of the sleeve 112. In several embodiments, the treatment device 101 does not include one of the sleeve 112 or the elongated member 102. In these and other embodiments, the treatment device 101 includes two or more elongated members (for example, as described herein with respect to FIG. 2). The treatment device 101 may include a lumen 22 to accept a guidewire or other guide rail, so that the device 101 may be positioned over the guide to a treatment site. The lumen 22 may extend along the elongated member 102 (or any component thereof) and terminate distally at a distal opening. The lumen 22 may also be configured to receive a visualization device therethrough.

The treatment device 101 further includes a treatment assembly 100 (or "assembly 100") carried by a distal portion of the elongated member 102. The treatment assembly 100 can comprise a capture portion 200 and a cutting portion 300, which may be integral with one another or separate components. The cutting portion 300 can comprise one or more cutting elements configured to cut through obstructive material in the vessel lumen as the treatment assembly 100 is moved axially along the lumen, thereby separating and/or releasing obstructive material from the vessel wall and/or from other obstructive material. The capture portion 200 can comprise one or more expandable mesh structures configured to engage, trap, or otherwise become enmeshed with obstructive material at the treatment site, before, during, or after engagement by the cutting portion 300. The capture portion 200 can comprise any of the capture portions 200 described herein, and the cutting portion 300 can comprise any of the cutting portions 300 described herein. Additional details regarding the capture portion 200 and the cutting portion 300 are described below.

Figure 2:
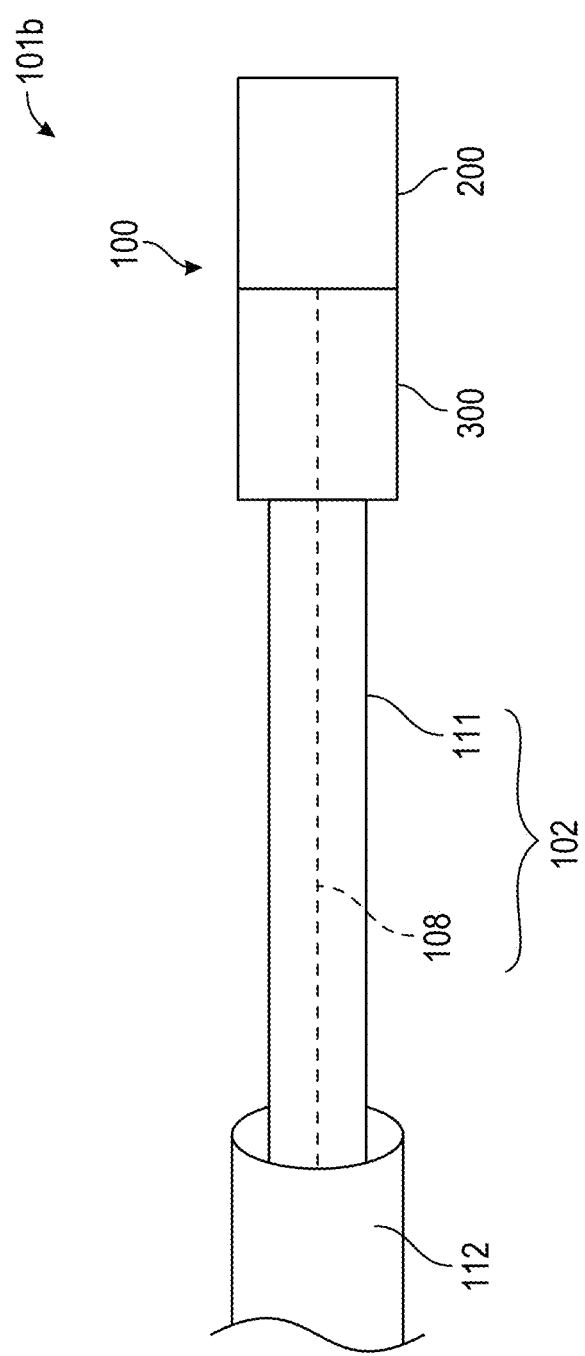
FIG. 2 schematically depicts a distal portion of a treatment system configured in accordance with several embodiments of the present technology.

The treatment assembly 100 is transformable between a low-profile state for delivery to the vessel lumen and a deployed (e.g., expanded) state, as detailed herein. As used herein with reference to the treatment assembly 100, "expanded" and "deployed" refer to a configuration of the treatment assembly 100 when one or both of the capture portion 200 and the cutting portion 300 are in a partially or fully expanded state. According to several embodiments described herein, the capture portion 200 and the cutting portion 300 are integrated into a single expandable device. In some of such embodiments, the treatment assembly 100 is self-expanding and coupled to a distal end portion of a single elongated member 102. In other embodiments in which the capture portion 200 and the cutting portion 300 are integrated into a single expandable device, the treatment assembly 100 (regardless of whether the treatment assembly 100 is self-expanding or requires activation) is coupled to at least two elongated members 108, 111, as shown in FIG. 2. The sleeve 112 may be positioned over the treatment assembly 100 to radially constrain and/or protect the treatment assembly 100 while being introduced to the vessel lumen. In such embodiments, the sleeve 112 is withdrawn proximally to expose the treatment assembly 100 to allow one or more portions of the treatment assembly 100 to expand.

According to several aspects of the technology, the capture portion 200 and the cutting portion 300 are independently deployable. In such embodiments, both the capture portion 200 and the cutting portion 300 can be self-expanding and be coupled to the same elongated member 102 or may be coupled to separate elongated members.

In some embodiments the capture portion 200 and the cutting portion 300 comprise separately-formed components, both carried by the distal region of the elongated member 102. One of many examples of such embodiments is shown in FIGS. 3A and 3B. In these embodiments, the capture portion 200 and the cutting portion 300 can be configured to collapse and expand independently of one another or via the same actuation mechanism. For example, the capture portion 200 can be a resilient structure configured to self-expand upon withdrawal of a sleeve 112, while expansion of the cutting portion 300 may require an additional actuation step by the operator (as detailed herein). Likewise, the cutting portion 300 can be a resilient structure configured to self-expand upon withdrawal of the sleeve 112, while expansion of the capture portion 200 may require an additional actuation step by the operator (as detailed herein). According to some examples, both the capture portion 200 and cutting portion 300 are resilient, self-expanding structures.

Referring still to FIG. 1, the handle 12 at the proximal portion 101a of the treatment device 101 can be permanently or detachably coupled to one or more of the elongated members (such as the sleeve 112, the elongated member 102, the inner member 108, the outer member 111, etc.). The handle 12 can include one or more actuators for controlling movement of one or more portions of the treatment assembly 100. For example, the handle 12 can include a first actuator 14 that is mechanically (e.g., via a push rod, push tube, and/or pull-wire) and/or electrically (e.g., via one or more wires) coupled to the capture portion 200 and a second actuator 16 that is mechanically (e.g., via a push rod, push tube, and/or pull-wire) and/or electrically (e.g., via one or more wires) coupled to the cutting portion 300. Activation of the first actuator 14, for example, can control one or more movements of the capture portion 200. In some embodiments, the first actuator 14 controls the axial movement, rotational movement, and/or radial expansion/contraction of some or all of the capture portion 200. In some embodiments, the second actuator 16 controls the axial movement, rotational movement, and/or radial expansion/contraction of some or all of the cutting portion 300. In some embodiments, the first actuator 14 controls the axial movement, rotational movement, and/or radial expansion/contraction of some or all of the capture portion 200. According to some aspects of the technology, the first and/or second actuators 14, 16 and/or a third actuator (not shown) controls the axial movement, rotational movement, and/or radial expansion/contraction of some or all of the capture portion 200 and some or all of the cutting portion 300. For example, the handle 12 can include an actuator that is configured to move the cutting portion 300 axially with respect to the capture portion 200 (or vice versa).

In some embodiments, the first and/or second actuator 14, 16, or an additional actuator (not shown) at the handle 12 is coupled to the sleeve 112 and configured to control axial and/or rotational movement of the sleeve 112. Such an actuator, for example, can be configured to axially advance or withdraw the sleeve 112 to selectively expose or cover all or a portion of the treatment assembly 100. In some embodiments, the first and/or second actuator 14, 16, or an additional actuator (not shown) at the handle 12 is coupled to the elongated member 102 and configured to control axial and/or rotational movement of the elongated member 102. In some embodiments, the first and/or second actuator 14, 16, or an additional actuator (not shown) at the handle 12 is coupled to the inner member 108 and configured to control axial and/or rotational movement of the inner member 108. In some embodiments, the first and/or second actuator 14, 16, or an additional actuator (not shown) at the handle 12 is coupled to the outer member 111 and configured to control axial and/or rotational movement of the outer member 111. The handle 12 can include more or fewer than two actuators (e.g., one actuator, three actuators, four actuators, five actuators, six actuators, etc.).

According to several aspects of the technology, the treatment system 10 optionally includes an introducer 103 for facilitating delivery of the treatment device 101 into the vessel lumen. The introducer 103 can comprise a proximal portion 103a, a distal portion 103b, a hub 105 at the proximal portion 103, and an elongated sheath 110 extending distally from the hub 105 to the distal portion 103b of the introducer 103. In some embodiments, the hub 105 is configured to be coupled to the suction source 18 and/or the fluid source 20 (e.g., via one or more ports). The hub 105 and sheath 110 can be configured to receive a portion of the treatment device 101 therethrough. For example, the treatment assembly 100, the elongated member 102, and/or the sleeve 112 can be configured to be inserted through the hub 105 and slidably positioned within a lumen of the sheath 110. In some embodiments, the hub 105 comprises a hemostatic valve. According to several embodiments, the introducer 103 includes a funnel at the distal end portion of the sheath 110. Several examples of such embodiments are depicted at FIGS. 12A-12C, 28A-28B, etc. The funnel can be configured to expand into apposition with the vessel wall proximate the distal end portion of the sheath 110, thereby preventing released obstructive material from traveling proximally of the introducer 103. In some embodiments, the system 10 does not include an introducer 103.

The treatment system 10 can optionally include a suction or aspiration source 18 (e.g., a syringe, a pump, etc.) configured to be fluidly coupled to a proximal portion of one or more of the introducer 103, the sleeve 112, and/or the elongated member 102 (and/or one or more subcomponents thereof) to apply negative pressure therethrough. In some embodiments, the treatment system 10 includes a fluid source 20 (e.g., a fluid reservoir, a syringe, pump, etc.) configured to be fluidly coupled to a proximal portion of one or more of the introducer 103, the sleeve 112, and/or the elongated member 102 (and/or one or more subcomponents thereof) to supply fluid to the treatment site. The fluid, for example, can be saline, contrast agents, a drug such as a thrombolytic agent, etc.

Actuators on the handle 12 or separate actuators connected directly to the suction source 18 and/or the fluid source 20 may control the application of aspiration and/or flushing through the system 10 to the treatment site. In some embodiments, a single actuator controls both aspiration and flushing.

In some methods of use, the system 10 can be introduced into the venous system from a proximal site (e.g., the common femoral vein or femoral vein) and advanced in a retrograde direction (against normal blood flow) to a treatment site in a vein of the patient's leg. The system 10 can also be introduced into the venous system from a distal site (e.g., a popliteal or more distal vein) and advanced in an antegrade direction (same direction as blood flow) towards the target treatment site. In some embodiments, the system 10 is introduced into an artery.

FIGS. 3A and 3B are top views of a distal portion 101b of a treatment device 101 with a treatment assembly 100 in various states of deployment, accordance with embodiments of the present technology. As shown in FIGS. 3A and 3B, the treatment assembly 100 can comprise a capture portion 200 and a cutting portion 300. The capture portion 200 and the cutting portion 300 can be independently deployable. For example, the capture portion 200 is shown in a deployed (e.g., expanded) state in FIGS. 3A and 3B, and the cutting portion 300 is shown in a collapsed state in FIG. 3A and a deployed state in FIG. 3B.

Figure 4:
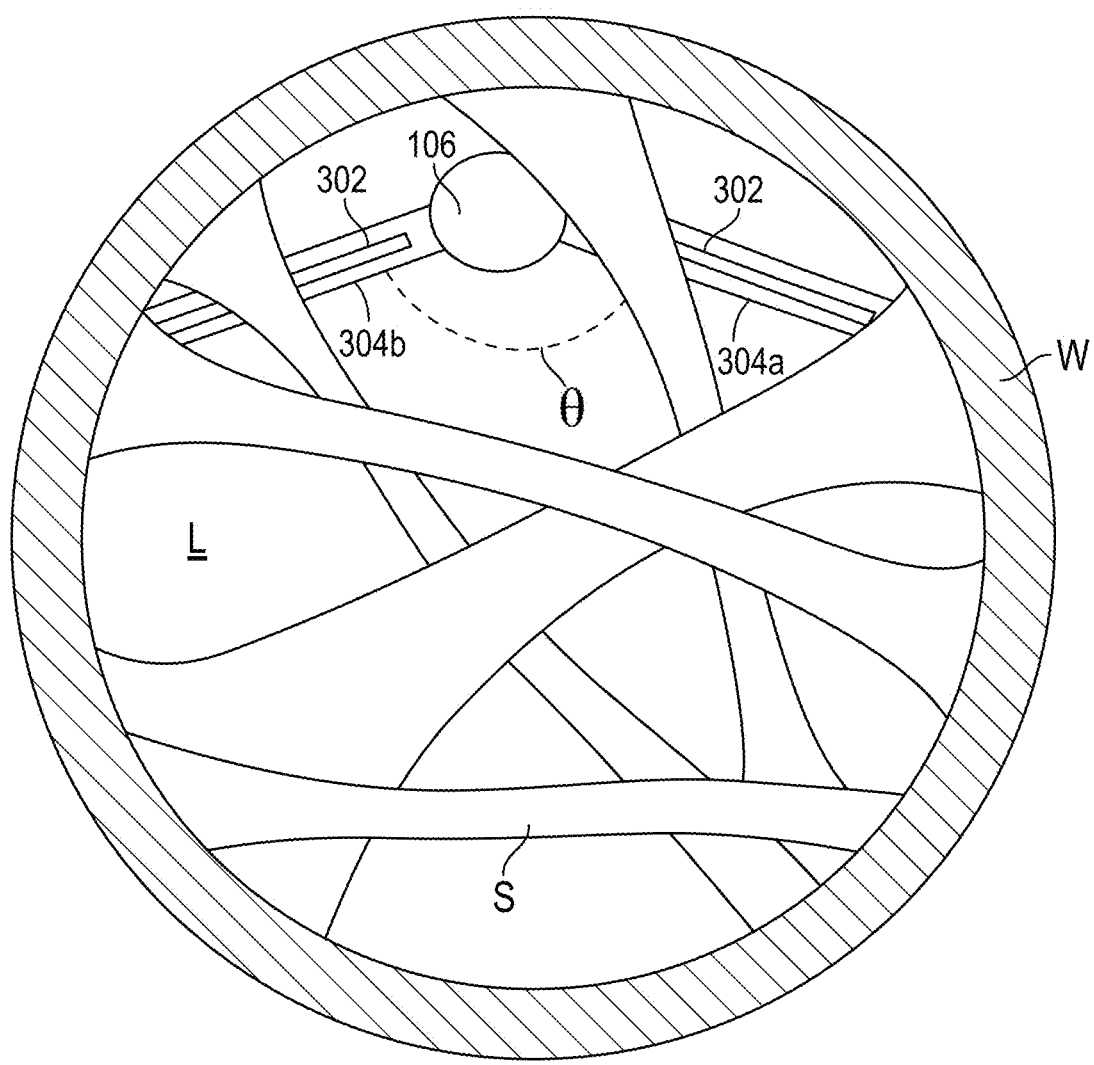
FIG. 4 schematically depicts an end view of a cutting portion of a treatment assembly configured in accordance with several embodiments of the present technology, shown positioned in a blood vessel lumen in an expanded state.

The cutting portion 300 can comprise one or more cutting elements 302 configured to cut through obstructive material in the vessel lumen as the treatment assembly 100 is moved axially along the lumen, thereby separating and/or releasing obstructive material from the vessel wall and/or other obstructive material. FIG. 4 schematically depicts the device positioned within a blood vessel. The arms 304 of the cutting portion 300 may be canted towards each other (rather than extending 180 degree apart) when expanded so that the arms 304 and attached blades 302 are at an angle θ that better approximates the curvature of the vessel wall. This geometry facilitates cutting obstructive material (such as chronic thrombus material) away from the curved vessel wall. In some embodiments, the angle between the two arms is less than 180 degrees. In some embodiments, the angle is between 135 and 180 degrees.

The capture portion 200 can comprise one or more expandable mesh structures configured to engage, trap, or otherwise become enmeshed with obstructive material at the treatment site. In some embodiments, for example as shown in FIGS. 3A and 3B, the cutting portion 300 can be positioned proximally of some or all of the capture portion 200 along the longitudinal axis of the assembly 100 and/or device 101 such that the portion(s) of the obstruction separated from the vessel wall by the axial movement of the cutting portion 300 are subsequently trapped in and/or become enmeshed with the capture portion 200 for removal from the patient's body. For example, in some embodiments, all or a portion of the cutting portion 300 is positioned distally of the obstructive material and move proximally, and in some embodiments all or a portion of the cutting portion 300 is positioned proximally of the obstructive material and is moves distally towards the capture portion 200.

As depicted in FIGS. 3A and 3B, in some embodiments the capture portion 200 and the cutting portion 300 comprise separately-formed components, both carried by the distal region of the elongated member 102. In such embodiments, the capture portion 200 and the cutting portion 300 can be configured to collapse and expand independently of one another or via the same actuation mechanism. For example, the capture portion 200 can be a resilient structure configured to self-expand upon withdrawal of a sleeve 112, while expansion of the cutting portion 300 may require an additional actuation step by the operator (as detailed herein). Likewise, the cutting portion 300 can be a resilient structure configured to self-expand upon withdrawal of the sleeve 112, while expansion of the capture portion 200 may require an additional actuation step by the operator (as detailed herein). According to some examples, both the capture portion 200 and cutting portion 300 are resilient, self-expanding structures.

In some embodiments of the present technology, for example as shown in FIGS. 3A and 3B, the elongated member 102 can comprise an outer member 111 and an inner member 108 positioned through a lumen of the outer member 111. A proximal end of each of the outer member 111 and the inner member 108 can be disposed at the handle so that the inner and outer members 108, 111 can be manipulated by an operator. In some embodiments, a distal end portion 200b of the capture portion 200 is coupled to the distal region of the inner member 108. In the embodiment shown in FIGS. 3A and 3B, for example, only the distal end portion 200b of the capture portion 200 is coupled to the distal region of the inner member 108 and the proximal end portion 200a is free to expand radially away from the inner member 108 when the sleeve 112 is withdrawn. As a result, when the capture portion 200 is in the expanded state, the proximal end portion 200a defines a proximal opening 206 through which obstructive material separated by the cutting portion 300 can pass to trap the obstructive material within an inner cavity defined by the capture portion 200. In some embodiments, only the proximal end portion 200a of the capture portion 200 is coupled to the inner member 108 and the distal end portion 200b is free and defines a distal opening in the expanded state. In some embodiments, both the proximal end portion 200a and the distal end portion 200b are coupled to the inner member 108.

Referring still to FIGS. 3A and 3B, a distal end portion 300b of the cutting portion 300 can be coupled to the inner member 108, and a proximal end portion 300a of the cutting portion 300 can be coupled to a distal end portion of the outer member 111. The distal end portion 300b of the cutting portion 300 can be coupled to the inner member 108 at a location that is distal to, generally aligned with, or proximal to the proximal terminus of the capture portion 200. In some embodiments, the distal end portion 300b is slidable along the inner member 108. In such embodiments, the inner member 108 may optionally include a distal and/or proximal stop to limit distal and/or proximal axial movement, respectively, of the cutting portion 300 along the inner member 108. In any case, movement of the outer member 111 relative to the inner member 108 can cause the cutting portion 300 to radially expand and collapse. For example, axial movement of the outer member 111 relative to the inner member 108 in a distal direction can cause the cutting portion 300 to radially expand, while axial movement of the outer member 111 relative to the inner member 108 in a proximal direction can cause the cutting portion 300 to radially collapse.

According to several embodiments of the present technology, the cutting portion 300 may comprise a tube with one or more regions removed along the distal portion to form expandable arms 304 (labeled individually as 304a and 304b). In some embodiments, the outer member 111 and the tube forming the cutting portion 300 are different portions of the same continuous tube. As previously described, distal movement of the outer member 111 with respect to the inner member 108 causes the arms 304 to buckle and/or bend outwardly away from the longitudinal axis of the elongated member 102, as shown in FIG. 3B.

The arms 304 can include one or more segments 306a, 306b, 308a, and 308b (referred to collectively as "segments 309") and one or more joints 310. The joints 310 can be positioned along the arms 304 between segments 309 and/or between a respective arm 304 and the rest of the tube from which the arms 304 are cut (e.g., the proximal and distal end portions of the arms 304). The joints 310 can be portions of the arms 304 that are configured to preferentially flex or bend relative to the segments 309 and/or the proximal and distal end portions of the tube. In some embodiments, one or more of the joints 310 can be formed by opposing recesses at a desired location along the arm 304 (e.g., a living hinge), and in other embodiments one or more of the joints 310 can be one or more small pins, elastic polymeric elements, mechanical hinges and/or other devices that enable one segment to pivot or bend relative to another.

In the embodiment shown in FIGS. 3A and 3B, each of the arms 304 includes a distal joint at its distal end portion, a proximal joint at its proximal end portion, and an intermediate joint positioned along the length of the respective arm 304 between the distal and proximal joints. In response to longitudinal stresses caused by relative axial movement of the inner and outer members 108, 110, the arms 304 deform into a predetermined shape biased by the configuration and/or relative positions of the joints 310. For example, in the illustrated embodiment, each of the arms 304, when deployed, includes a generally linear distal segment 306a, 306b and a generally linear proximal segment 308a, 308b. In some embodiments, each of the arms 304, when deployed, includes a generally curved distal segment 306a, 306b and/or a generally curved proximal segment 308a, 308b.

The cutting portion 300 can include one or more cutting elements, such as blades 302, fixedly coupled to one or more segments of the arms. In the embodiment shown in FIGS. 3A and 3B, each of the blades 302 has a sharpened edge that faces proximally when the cutting portion 300 is in the deployed and/or expanded state. The blades 302 may comprise a first material while the arms 304 and/or cutting portion 300 may comprise a second material different than the first material. For example, the blades 302 may comprise stainless steel while the arms 304 and/or cutting portion 300 may comprise a resilient and/or superelastic metal alloy, such as Nitinol, a cobalt-chromium alloy, and others. In some embodiments, the blades 302 comprise the same material as the arms 304. According to several embodiments, the cutting elements are not separately-formed structures and instead are formed of a sharpened surface of the cutting portion 300.

Figure 5:
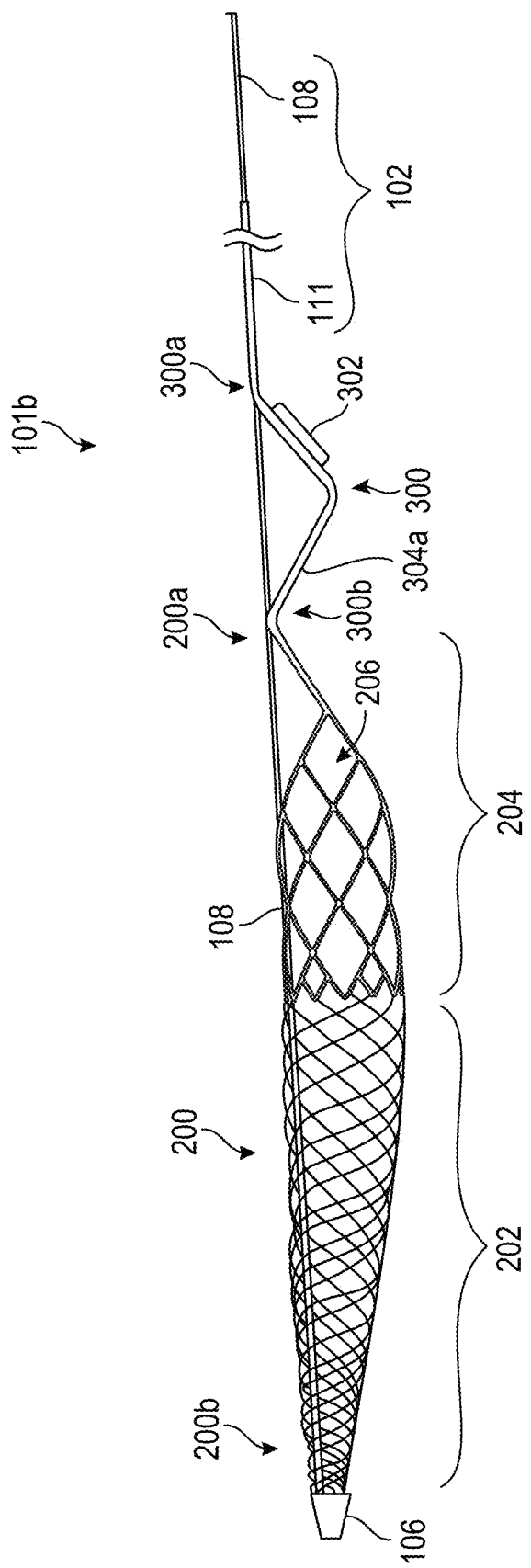
FIG. 5 is a side view of a treatment assembly configured in accordance with several embodiments of the present technology, shown in an expanded state.

FIG. 5 is a side view of a distal portion 10b of a treatment system 10 configured in accordance with several embodiments of the present technology, with the treatment assembly 100 shown in an expanded state. The assembly 100 can comprise an elongated member 102 and a cutting portion 300 that are generally similar to the elongated member 102 and cutting portion 300 discussed above with reference to FIGS. 3A and 3B. The capture portion 200 shown in FIG. 5 can be generally similar to the capture portion 200 shown in FIGS. 3A and 3B, except the capture portion 200 shown in FIG. 5 includes a flexible braided distal region 202 and a more rigid proximal region 204 formed of a laser-cut tube or sheet of material. The tube forming the proximal region 204 can be continuous with or separate from a distal region of the cutting portion 300. The proximal region 204 can have a greater chronic outward force and/or radial resistive force as compared to the distal region 202, which can be beneficial for maintaining the patency of the proximal opening 206 once the assembly 101 and/or device 101 is deployed. In some embodiments, the cutting portion 300 may be fixed to or integral to the capture portion 200. For example, the proximal, open end region 204 of the capture portion 200 may be constructed from a cut nitinol tube. The main structure of the cutting portion 300 may also be constructed from a cut nitinol tube, as described above. The nitinol tube of region 204 and of cutting portion 300 may be the same nitinol tube with two sections of cut pattern. Alternately, nitinol tube of region 204 and of cutting portion 300 may be two separate tubes which are mechanically coupled, glued, soldered or welded, to fixedly couple the capture portion 200 with the cutting portion 300.

Figure 6:
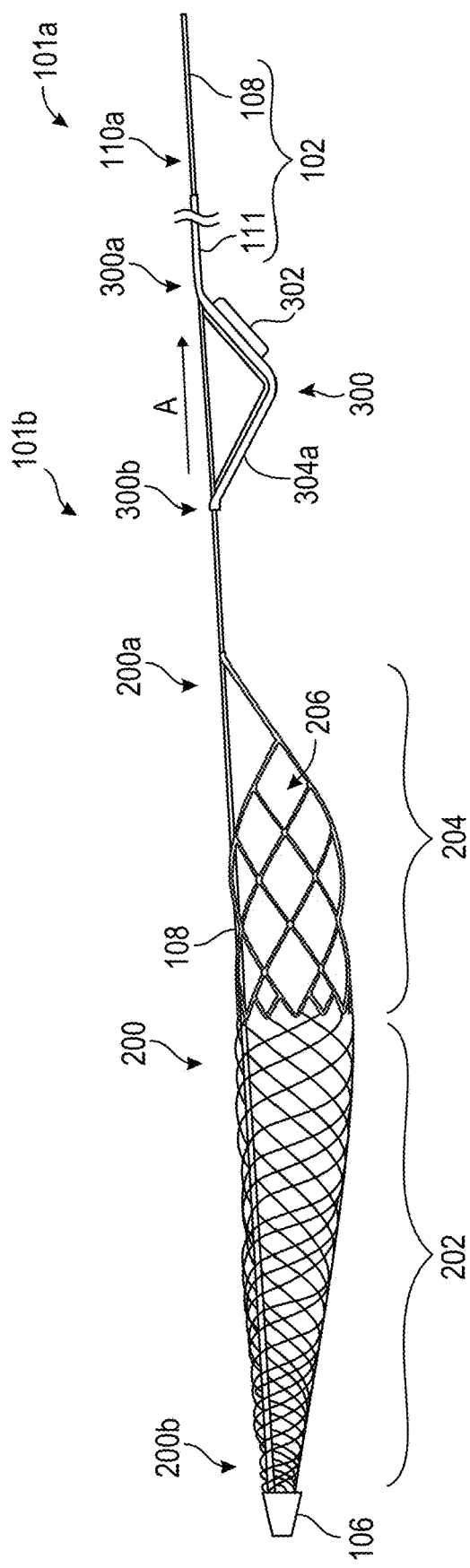
FIGS. 6 and 7 are side views of a treatment assembly configured in accordance with several embodiments of the present technology.
Figure 7:
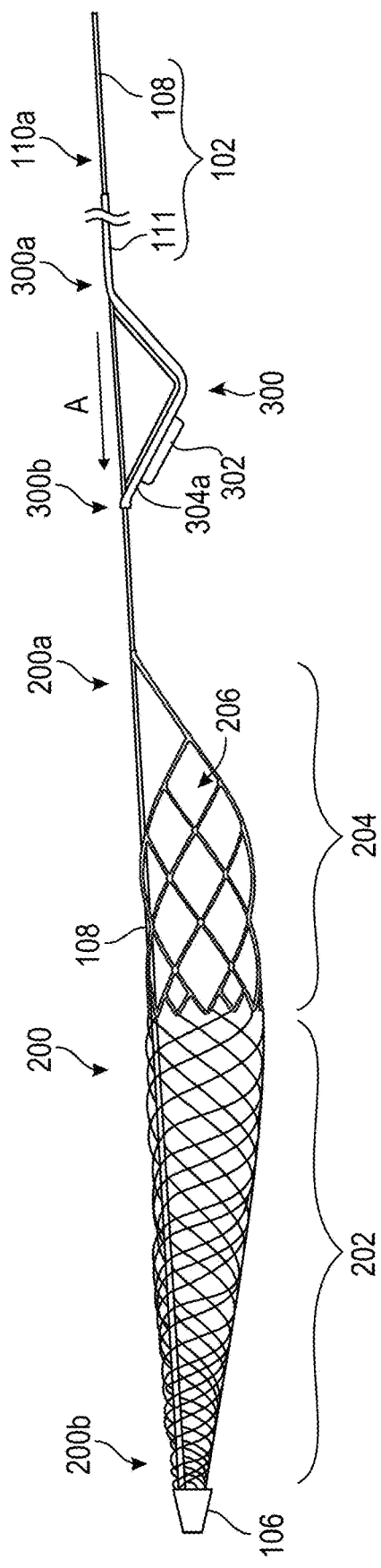

FIGS. 6 and 7 shows a distal portion of a device 101 configured in accordance with several embodiments of the present technology. As shown in FIGS. 6 and 7, in some embodiments the cutting portion 300 and the capture portion 200 are separate components that are spaced apart and slidably coupled. In this embodiment, the blades of the cutting portion 300 of assembly 100 and/or device 101 can face proximally or face distally, depending on how the capture portion 200 and cutting portion 300 are configured to be used with respect to each other. In one variation, shown in FIG. 6, the cutter is oriented in the distal direction. According to some methods of use, the treatment assembly 100 is initially positioned in the blood vessel lumen such that both the capture portion 200 and cutting portion 300 are distal to the obstructive material. The two portions 200, 300 can be expanded, for example, by retraction of a sheath, or by any of the expansion mechanisms described herein. The cutting portion 300 can be pulled proximally to cut through the obstructive material, and subsequently the capture portion 200 can be pulled proximally cut gather the cut obstructive material. In some embodiments, the cutting portion 300 and capture portion 200 can alternately and/or simultaneously be pulled back to cut and capture the obstructive material.

In another variation, as shown in FIG. 7, the blades 302 on the cutting portion face distally. According to some methods of use, the treatment assembly 100 is initially positioned in the blood vessel lumen such that the capture portion 200 is distal to the obstructive material and the cutting portion 300 is proximal to the obstructive material In use, the cutting portion 300 can be moved axially towards the capture portion 200 to separate obstructive material from the wall and push the obstructive material into the capture portion 200.

Figure 8:
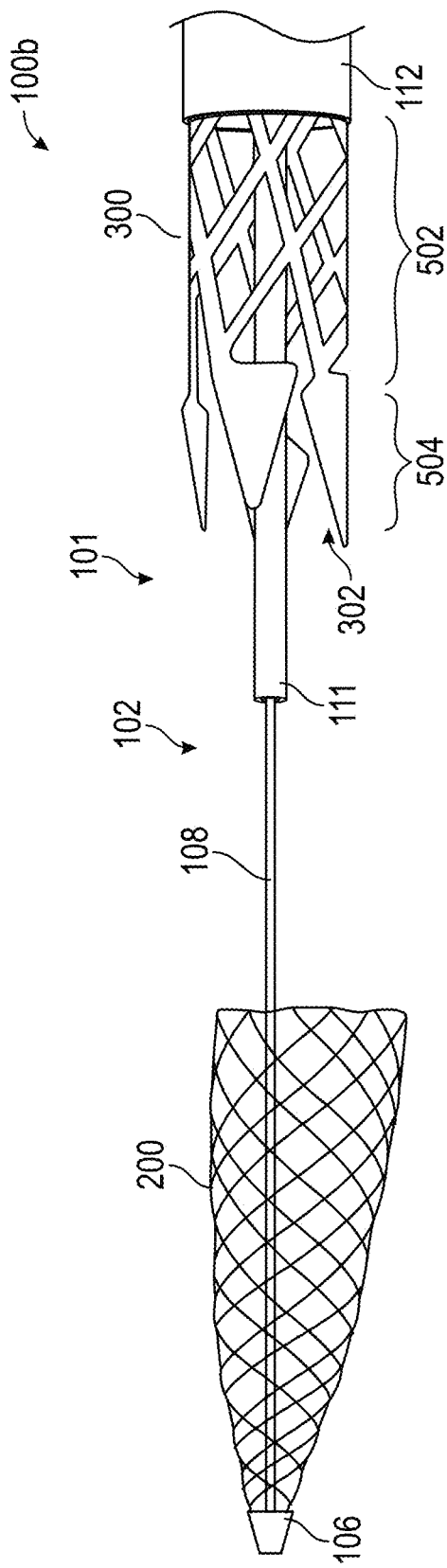
FIGS. 8 and 9A are side views of a treatment assembly configured in accordance with several embodiments of the present technology, shown in an expanded state.

In some embodiments, the cutting portion 300 of the assembly 100 may be an expandable tubular structure with integrated cutting elements. FIG. 8, for example, shows an assembly 100 with a cutting portion 300 comprising a substantially tubular, stent-like portion 502 and a plurality of arms 504 extending away from the stent-like portion 502 in a distal direction. The cutting portion 300 can further include a plurality of cutting elements 302, each disposed at an end portion of a corresponding arm 502. For example, in some embodiments, the cutting portion 300 is constructed from a cut nitinol tube with integrated cutting elements 302 (such as blades) arranged in a circular array. The arms 504 and cutting elements 302 may be spaced apart about a circumference of the cutting portion 300 such that the cutting portion 300 is configured to create a cut that extends circumferentially around the blood vessel wall. Such a feature may be advantageous in some situations due to the amount of obstructive material in the vessel and/or the difficulty with separating the obstructive material from the vessel wall. The cutting edge of the cutting elements 302 may be sharpened and configured to mechanically cut and/or otherwise modify the obstructive material. Additionally or alternatively, the cutting edge of the cutting elements may be configured to chemically cut and/or otherwise modify the obstructive material.

In some embodiments, one, some, or all of the arms 504 are tapered. In some embodiments the arms 504 are not tapered and/or have a generally constant width and/or arc length along their lengths. In a collapsed state (not shown), the distal end portions can be circumferentially spaced apart while the intermediate portions of the projections circumferentially overlap with the circumferentially adjacent projections. In an expanded state (FIG. 8), the end portions of the arms 504 can be circumferentially spaced apart by a greater arc length than when the device was in the collapsed state, and the intermediate portions circumferentially overlap to a lesser extent than in the collapsed state or do not overlap at all.

As shown in FIG. 8, the arms 504 and/or cutting elements 302 can be directed distally towards the capture portion 200. In several of such embodiments, the cutting portion 300 can be configured to move axially relative to the capture portion 200. For example, the cutting portion 300 can be slidably coupled to an outer elongated member 111 while the capture portion 200 can be coupled to an inner elongated member 108. Other configurations that allow independent movement of the capture portion 200 and the cutting portion 300 are possible. In use, the cutting portion 300 can be deployed and/or otherwise positioned proximally of the obstructive material with all or a portion of the capture portion 200 positioned distally of the obstructive material. The cutting portion 300 can be pushed distally to cut the obstructive material and separate the obstructive material from the vessel wall and/or from other obstructive material.

Figure 9A:
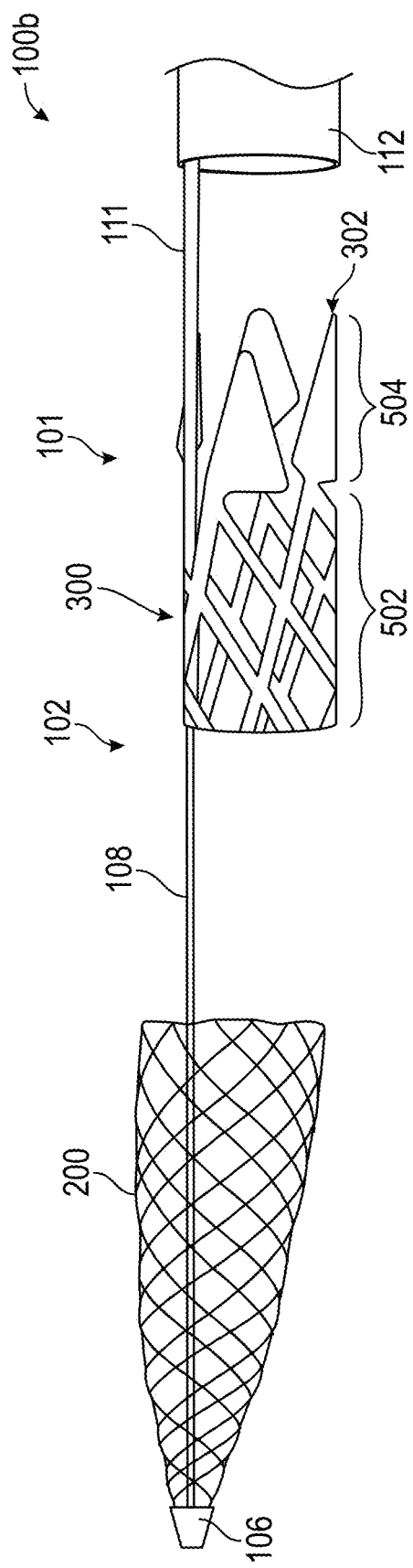
Figure 9B:
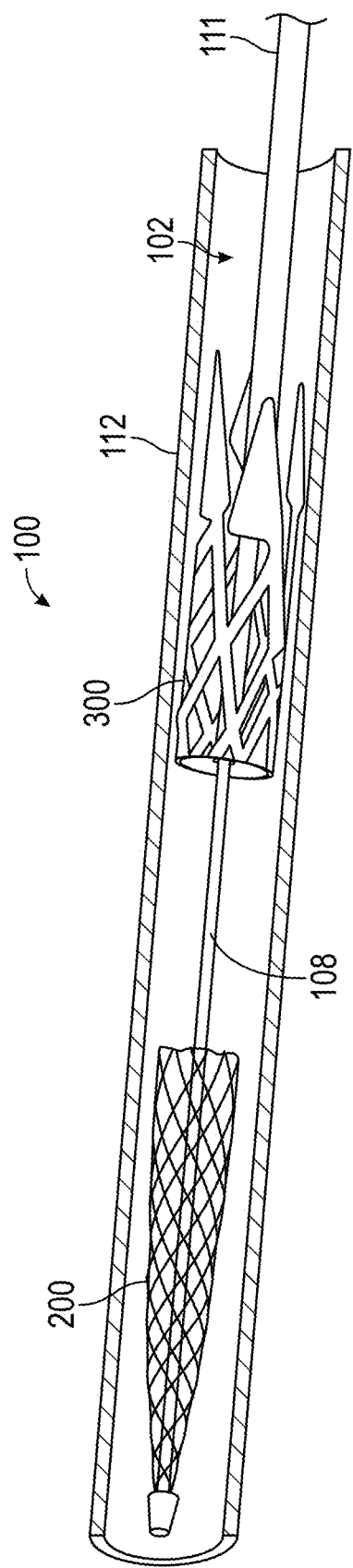
FIG. 9B is a side view of a treatment assembly configured in accordance with several embodiments of the present technology, shown in a collapsed state.

FIG. 9A shows a treatment assembly 100 that is generally similar to the treatment assembly 100 of FIG. 8, except in FIG. 9A the plurality of arms 504 extend away from the stent-like portion 502 in a proximal direction. In use, the capture portion 200 and cutting portion 300 can be deployed and/or otherwise positioned distally of the obstructive material and pulled proximally to cut the obstructive material. FIG. 9B depicts the treatment assembly 100 in a collapsed state within a sleeve 112 (shown in cross-section).

In some embodiments where the capture portion 200 and cutting portion 300 are separately-formed components, the capture portion 200 and the cutting portion 300 can be fixed to one another such that axial and/or rotational movement of one of the portions 200, 300 causes axial movement of all or a portion of the other portion 200, 300. For example, a distal end portion 300b of the cutting portion 300 can be fixedly coupled to a proximal end region 200a of the capture portion 200. If both the cutting portion 300 and the capture portion 200 are fairly rigid structures with high column strength (such as a laser-cut tube or sheet of material), axial movement of the cutting portion 300 will cause axial movement of the entire capture portion 200 and vice versa. If one of the capture portion 200 or the cutting portion 300 is a more flexible structure with low column strength (such as a braid) while the other is a more rigid structure, axial movement of the more rigid structure may cause an end region of the more flexible structure to collapse axially, while axial movement of the flexible structure may not cause any axial movement of the more rigid structure.

According to several embodiments, the capture portion 200 and the cutting portion 300 can be rotated and/or moved axially independently of one another. For example, the elongated member 102 can comprise a first elongated member coupled to the capture portion 200 and a second elongated member coupled to the cutting portion 300. The first and second elongated members can be configured to move axially relative to one another and/or rotate relative to one another (for example, where one elongated member is received within a lumen of the elongated member), thereby causing axial movement and/or rotation of the corresponding attached capture and cutting portions 200, 300. In some embodiments, the capture portion 200 and the cutting portion 300 can be mounted to the same elongated member, but one of the capture portion 200 or the cutting portion 300 is fixed axially and/or rotationally to the elongated member while the other is free to slide along and/or rotate about the elongated member. In some embodiments the capture portion 200 and cutting portion 300 are both fixed axially and/or rotationally to the elongated member.

In any of the embodiments in which the capture portion 200 and the cutting portion 300 are separately-formed components, the capture portion 200 and the cutting portion 300 may be configured to radially expand and collapse independently of one another or via the same actuation mechanism, as discussed herein.

Figure 10:
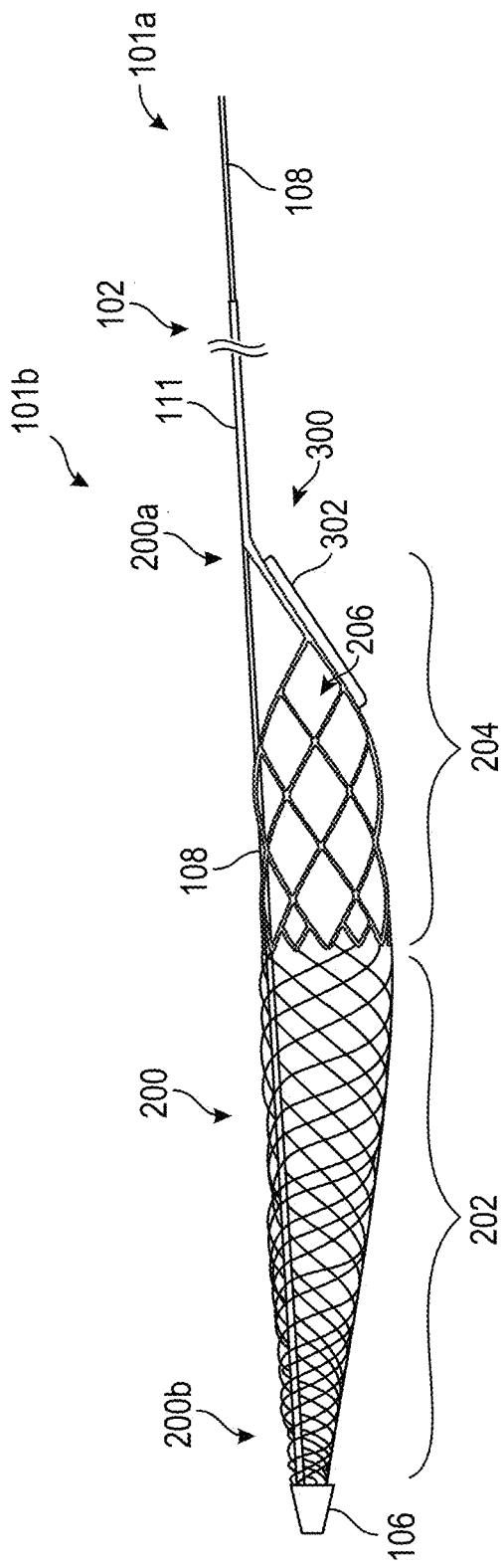
FIG. 10 is a side view of a treatment assembly configured in accordance with several embodiments of the present technology.

In some embodiments of the present technology, the cutting portion 300 is integrated within the structure of the capture portion 200 or vice versa. For example, as shown in FIG. 10, the capture portion 200 can have one or more cutting elements facing proximally along a proximal surface of the capture portion and configured to cut obstructive material when the device is pulled back. The cutting elements may be angled with respect to the longitudinal axis of the elongated member 102 to optimize the ability of the blades to slide through the tough material as the device is pulled proximally. The cutting elements can be one or more separately-formed blades coupled to the proximal surface of the capture portion 200. For example, the cutting elements can be separately-formed blades 302 that are mechanically attached to the capture portion 200 (for example via the latching configuration described with respect to FIGS. 19A and 19B). In such embodiments, the struts defining the proximal opening 206 of the capture portion 200 can have slots or other features to mechanically lock the blades 302 in place relative to the struts. Additionally or alternatively, the cutting elements can be formed of the same material and/or structure as the capture portion 200. For example, the cutting elements can be formed of a sharpened, proximally facing surface of the capture portion 200.

Figure 11:
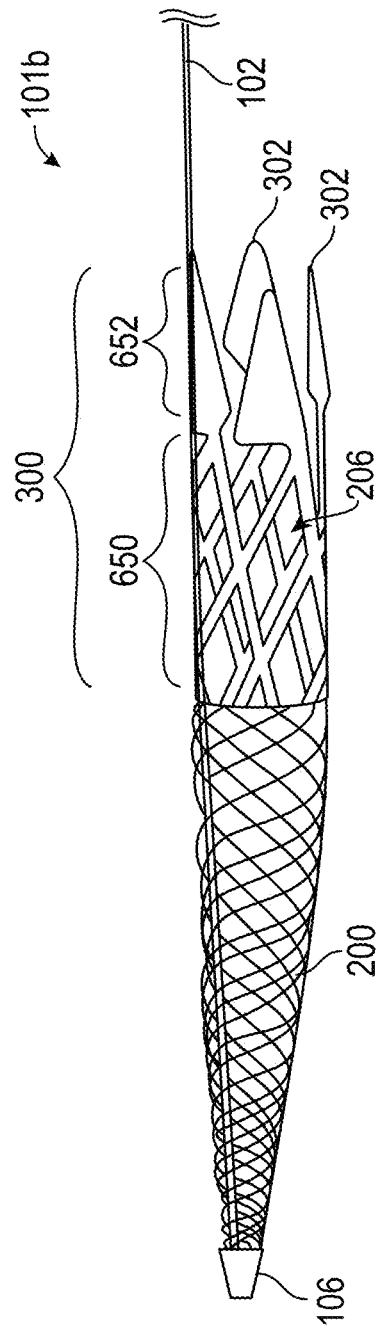
FIG. 11 is a side view of a treatment assembly configured in accordance with several embodiments of the present technology, shown in an expanded state.

In some embodiments, for example as shown in FIG. 11, the cutting elements and/or projections carrying the cutting elements are constructed from the same metal tube that comprises the proximal portion 204 of capture portion 200 and include protruding tapered elements that furl together when collapsed, similar to FIGS. 8-9B. While the assembly 100 in FIG. 11 shows a capture portion 200 comprising a braid, in some embodiments the capture portion 200 may comprise a laser-cut stent.

Regarding FIGS. 8, 9A, 9B, 11, 27A, 27B, 28A, and 28B, one, some, or all of the projections (such as arms 504, arms 652, projections 1502, etc.) can include a cutting element 302. The cutting element can be coupled to the projection (such as a blade) or the cutting element can be cut into the tube forming the treatment assembly 100. In some embodiments, the cutting elements are positioned at the distal end portions of the projections. In these and other embodiments, the cutting elements may be positioned along all or a portion of one or both side surfaces of a given projection.

When the treatment assembly 100 is in a collapsed state, the projections can be compressed together, and when the treatment assembly 100 is in an expanded state the projections can expand outward to contact and/or conform to the vessel wall. When the treatment assembly is pulled into and through the obstructive material, the cutting elements cut the obstructive material away from the vessel wall. The cutting elements may be configured to be angled such that pulling the device causes the cutting surface to slice across the obstructive material to improve the cutting action. The distal and/or side edges of one, some, or all of the projections 312 and/or blades can be generally linear, generally curved, serrated, and other have suitable configurations.

Figure 12C:
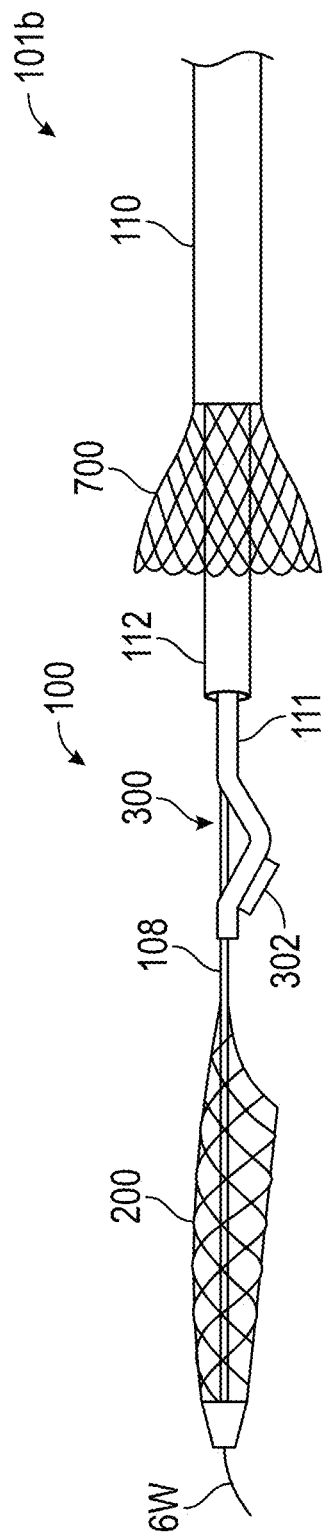

The devices and systems of the present technology can optionally include a sheath 110 with a self-expanding funnel configured to extend distally from the distal opening of the sheath 110. Such a feature can be beneficial for corralling the captured obstructive material into the sheath 110 as the treatment assembly 100 is withdrawn into the sheath 110. An example system 10 including a funnel 700 is shown in FIGS. 12A and 12B. As shown in FIG. 12A, the treatment device 101 with treatment assembly 100 can be delivered in a collapsed state through a sheath 110 with the funnel 700 in an expanded state. Once positioned, the sleeve 112 can be retracted to cause the treatment assembly to expand. FIG. 12B shows the sleeve 112 partially retracted to show the capture portion 200 of the treatment assembly expanded 100. FIG. 12C shows the sleeve 112 fully retracted to show the cutting portion 300 of the treatment assembly 100 expanded. Additionally or alternatively, aspiration may be applied to the sheath 110 with or without a funnel to further reduce the risk of embolization. The funnel 700 can be used with any of the systems detailed herein.

A. Example Capture Portions

Several capture portion configurations are shown and described with respect to FIGS. 13-16. The cutting portions 300 are not shown in FIGS. 13-16 for ease of viewing the capture portions 200. It will be appreciated that the present disclosure is not limited to the capture portions 200 depicted in the drawings.

Figure 13:
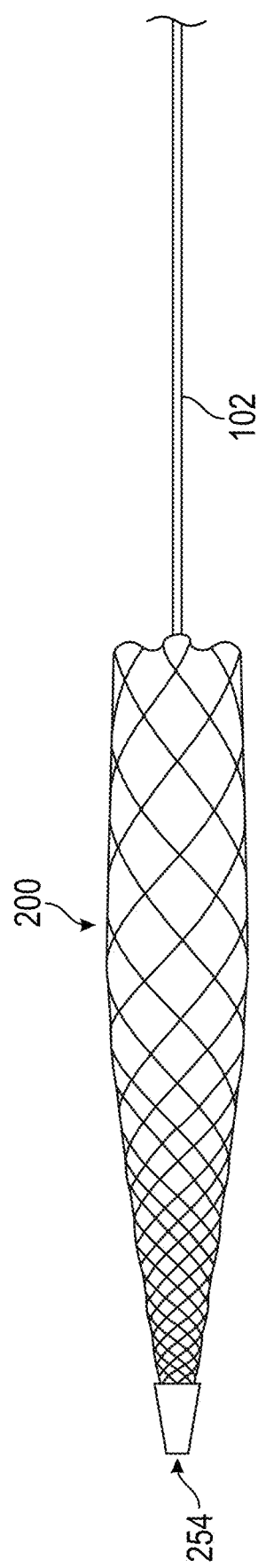
FIGS. 13-16 are side view of capture portions configured in accordance with several embodiments of the present technology.

FIG. 13 shows a capture portion comprising a braided or woven capture portion 200 having a closed distal end portion and an opening at its proximal end portion. The braid has a tapered shape with a cross-sectional dimension that decreases in a distal direction. The distal end of the braid may be cinched together with a tip component 245, that constrains the ends of the braid wires together. The tip component 245 may have a tapered or rounded distal edge to reduce the trauma to vessel wall as the assembly 100 and/or device 101 is delivered to the treatment site, and to facilitate crossing the device through chronic thrombus site. The tip component 254 may also affix the actuation member 102 to the distal end of the capture device.

Figure 14:
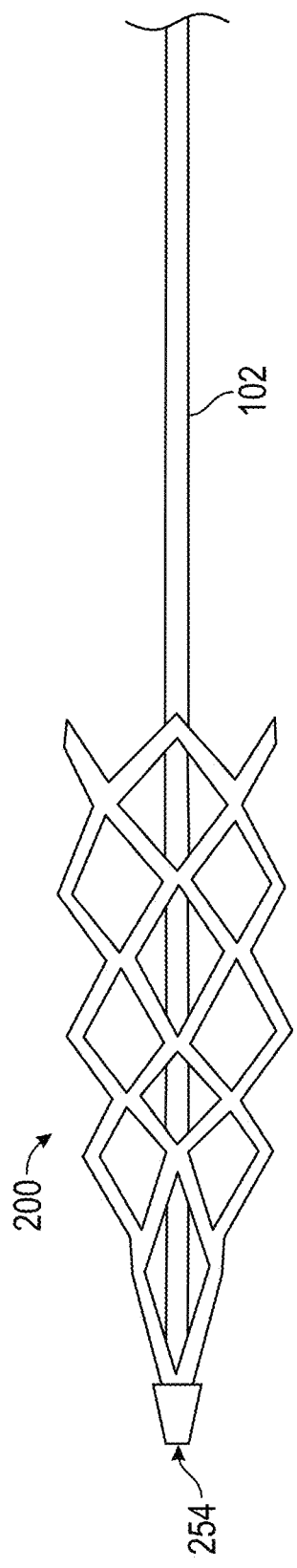

FIG. 14 shows a capture portion 200 comprising a laser-cut mesh structure having a closed distal end portion and an opening at its proximal end portion. The mesh structure has a tapered shape with a cross-sectional dimension that decreases in a distal direction. The closed distal portion may be cinched closed with a tip component 245 that constrains the ends of the cut tube pattern together. As above, the tip component 245 may have a tapered or rounded distal end and also may be used to affix the elongated member 102 to the closed end of portion member 200.

Figure 15:
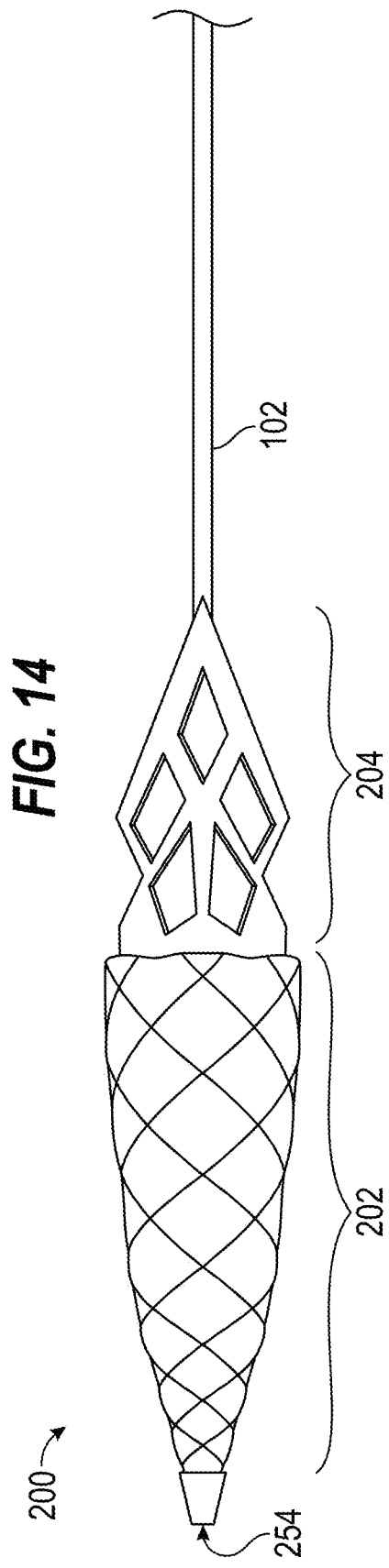

FIG. 15 shows a capture portion 200 comprising a flexible, tapered distal region 202 coupled to a more rigid proximal region 204. The distal region can comprise a braid, and the proximal region 204 can comprise a laser-cut tube or sheet of material. The proximal region 204 can have a greater chronic outward force and/or radial resistive force as compared to the distal region 202, which can be beneficial for maintaining the patency of the proximal opening 206 once the assembly 100 is deployed in the vessel lumen.

In any of the embodiments disclosed herein, the capture portion 200 can include an open cell framework or body. According to several embodiments, the entrance to the capture portion 200 is slanted to facilitate capture of the obstructive material into the capture portion 200. In some embodiments, a distal portion 200b of the capture portion 200 is generally tubular (e.g., cylindrical), and the proximal end portion 200a of the capture portion 200 tapers proximally down to the elongated member 102 (or component thereof). Likewise, the proximal end portion 200a of the capture portion 200 can be generally tubular (e.g., cylindrical), and the distal portion 200b of the capture portion 200 tapers distally down to the elongated member 102 (or component thereof).

In some embodiments, the capture portion 200 can have an open proximal end and a closed distal end. In some embodiments, the capture portion 200 has an open proximal end and an open distal end. In some embodiments, the capture portion has a closed proximal end and an open distal end.

Figure 16:
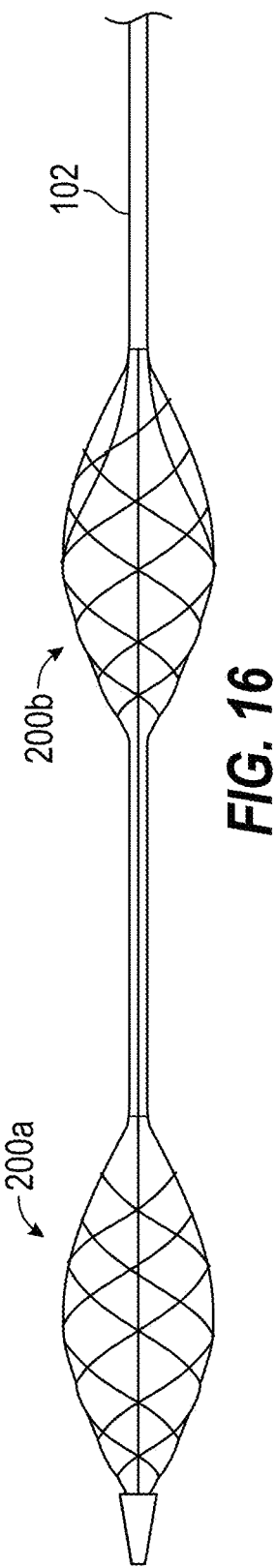

In some embodiments, the capture portion 200 comprises a single expandable mesh structure. In some embodiments, for example as depicted in FIG. 16, the capture portion 200 comprises a plurality of expandable structures 200a, 200b. The different structures can have the same or different shapes, can expand to the same or different maximum cross-sectional dimensions, and/or can comprise the same or different type of mesh structure (e.g., a braid, a laser-cut tube, a laser-cut sheet, a weave, etc.).

In some embodiments, the capture portion 200 comprises a mesh structure formed of an elastic or spring material (e.g.

stainless steel or cobalt chromium alloy), superelastic material (e.g., Nitinol,) or other resilient or self-expanding material configured to self-expand when released from the restraining sleeve 112. For example, in some embodiments the mesh is a self-expanding stent and/or stentriever. According to several embodiments, the mesh structure is a laser-cut tube or sheet of material. The material, for example, can comprise a resilient, elastic, and/or superelastic metal alloy or polymer. In some embodiments, the mesh structure comprises a plurality of braided wires (e.g., filaments, threads, sutures, fibers or the like) that have been interwoven to form a structure having openings. The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polylactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium, or alloys of any of these metals. In certain embodiments, metal filaments may be highly polished and/or surface treated to further improve their hemocompatibility. The capture portion 200 can be constructed solely from metallic materials without the inclusion of any polymer materials, solely from polymer materials without the inclusion of any metallic materials, or a combination of polymer and metallic materials.

In some embodiments, some or all of the wires of the capture portion 200 are drawn-filled tube ("DFT") wires having a radiopaque core (e.g., platinum, tantalum, gold, tungsten, etc.) surrounded by an elastic or superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. Moreover, some or all of the wires may have a wire diameter of about 0.003 inches to about 0.015 inches (e.g., 0.008 inches, 0.009 inches, 0.01 inches, etc.). In some embodiments, all of the wires have the same diameter, and in other embodiments some of the wires have different diameters.

B. Example Cutting Portions

Figure 17A:
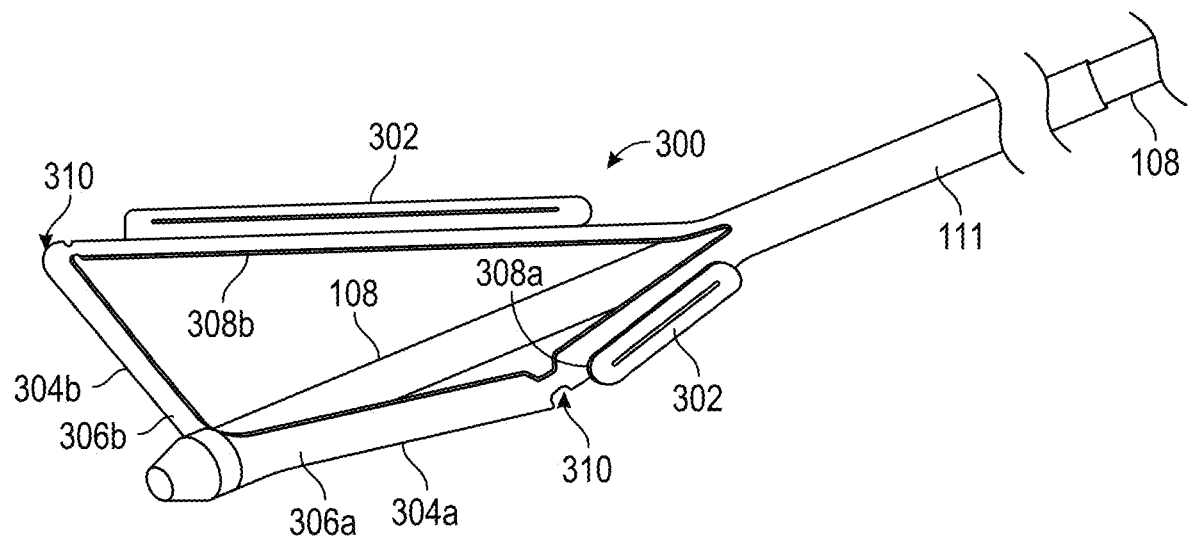
FIG. 17A is an isometric view of a cutting portion configured in accordance with the present technology, shown in an expanded state.

According to several embodiments of the present technology, the cutting portion 300 may comprise separate cutting element, such as blades, attached to an expandable structure forming the cutting portion 300. As described previously, the cutting portion may face distally or proximally as shown in FIGS. 6 and 7, and also in FIGS. 8 and 9A, respectively. The cutting portion may also be and may be fixed to capture portion as shown in FIGS. 10 and 11. The expandable structure can be configured to angle the cutting elements such that, when the device is pulled towards and then through the obstructive material, the cutting elements cut the obstructive material away from the vessel wall. Continued withdrawal of the device then pulls the obstructive material into the capture portion 200. An example of a such an expandable structure is shown in FIG. 17A. Similar to the cutting portion 300 described with respect to FIGS. 3A and 3B, the cutting portion 300 in FIG. 17A can be formed of a tube having two or more longitudinally-extending slots that create at least two arms 304 configured to bend radially outwardly when the tube is shortened. The longitudinal slots can be formed such that the arms 304 have joints 310 that bend when the arms 304 are expanded.

Figure 17B:
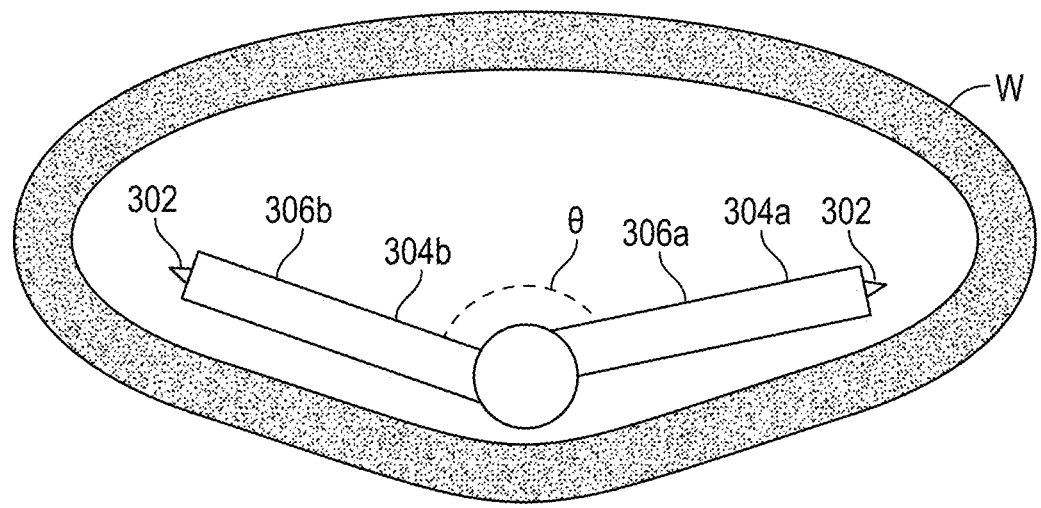
FIG. 17B is an end view of the cutting portion shown in FIG. 17A shown positioned within a blood vessel lumen in an expanded state.

As shown in FIG. 17B, the arms 304 of the cutting portion 300 may be canted towards each other (rather than extending 180 degree apart) when expanded so that the arms 304 and attached blades 302 are at an angle θ that better approximates the curvature of the vessel wall. This geometry facilitates cutting obstructive material (such as chronic thrombus material) away from the curved vessel wall. In some embodiments, the angle between the two arms is less than 180 degrees. In some embodiments, the angle is between 135 and 180 degrees.

Figure 18A:
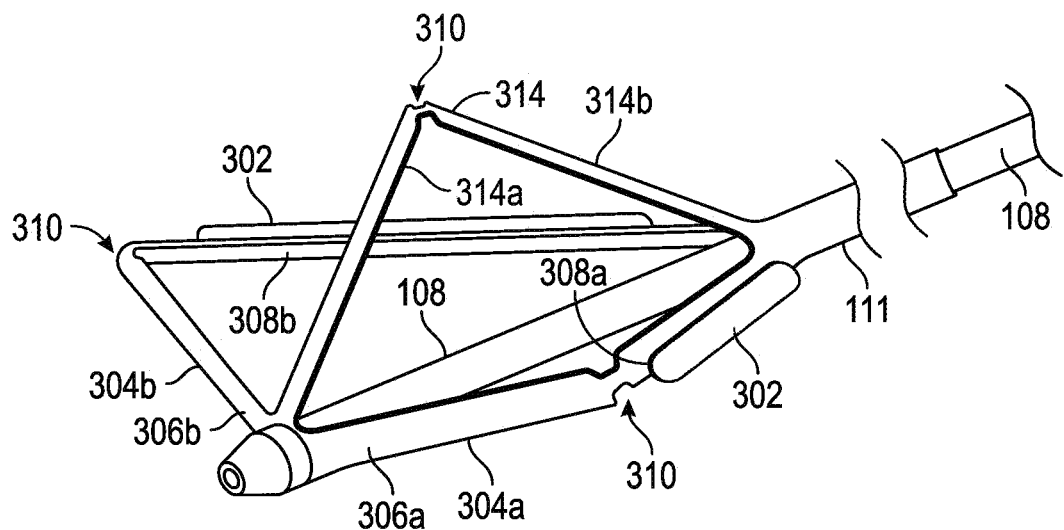
FIG. 18A is an isometric view of a cutting portion configured in accordance with the present technology, shown in an expanded state.
Figure 18B:
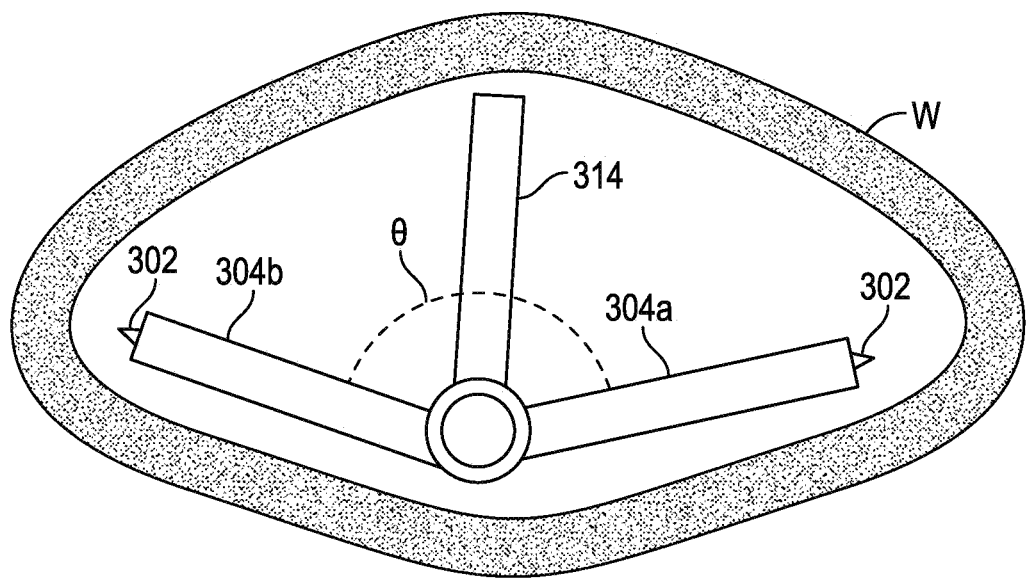
FIG. 18B is an end view of the cutting portion shown in FIG. 18A shown positioned within a blood vessel lumen in an expanded state.

As shown in FIG. 18A, in some embodiments the cutting portion 300 can include a positioning arm 314 disposed circumferentially between the two arms 304 having cutting elements. As depicted in FIG. 18B, when the cutting portion 300 is in an expanded state, the positioning arm 314 pushes against a portion of the vessel wall opposite the elongated member 102 and improves the position of the cutting elements for cutting and/or separating the obstructive material from the vessel wall.

Figure 19A:
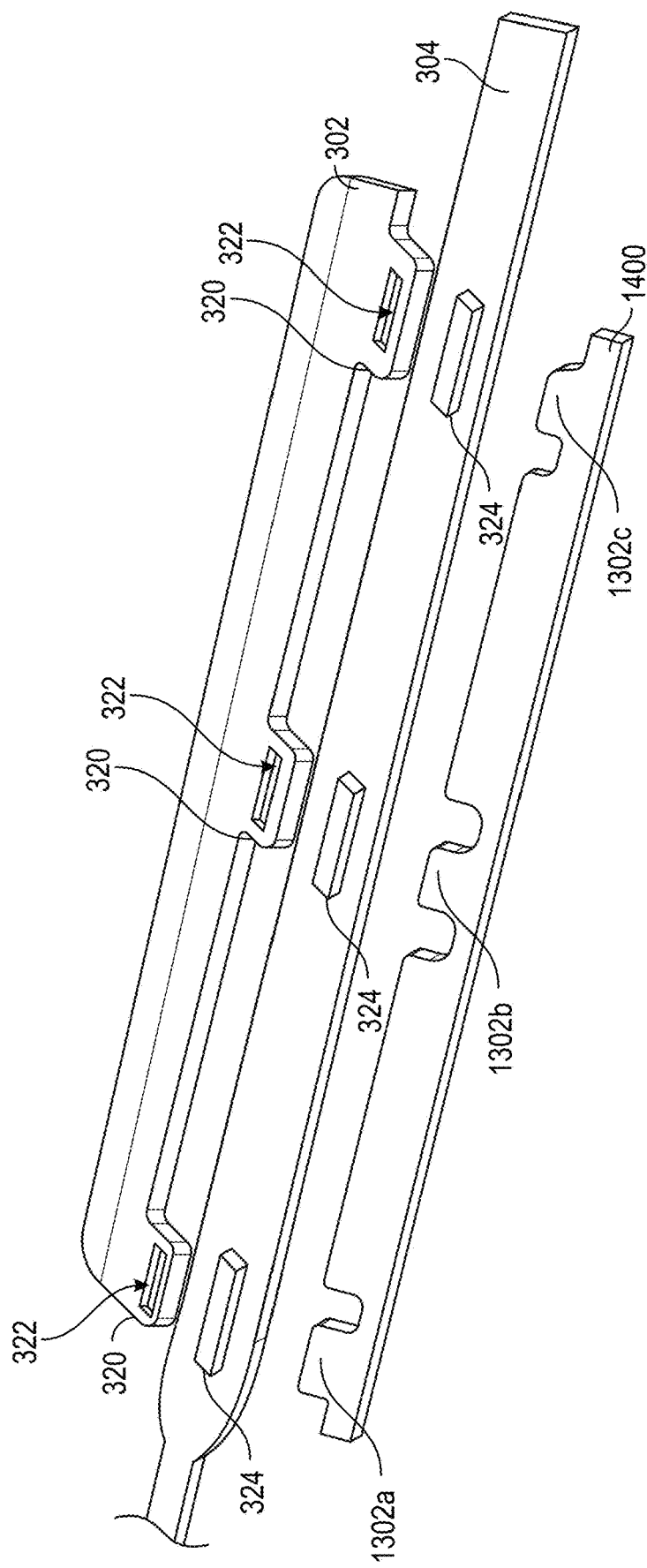
FIG. 19A is an exploded view of a blade assembly configured in accordance with several embodiments of the present technology.
Figure 19B:
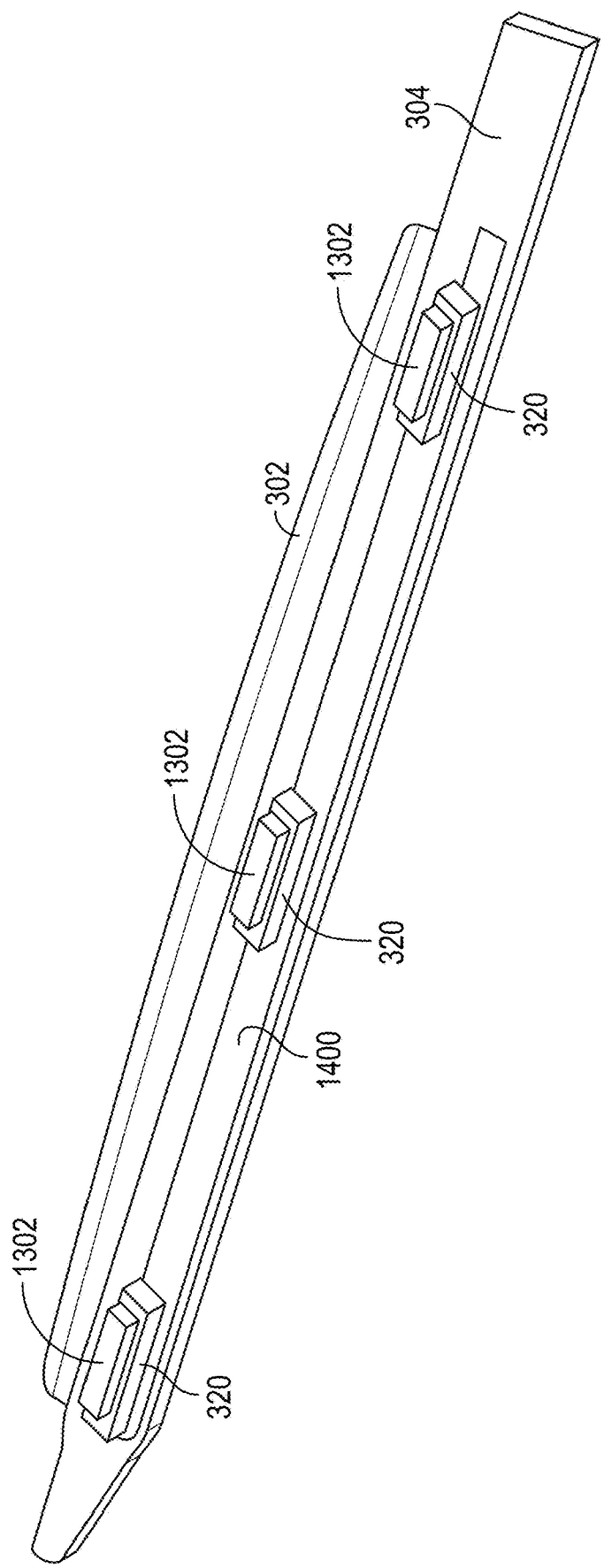
FIG. 19B is an assembled view of a blade assembly configured in accordance with several embodiments of the present technology.

FIGS. 19A and 19B are exploded and assembled views, respectively, of an example blade attachment assembly configured in accordance with several embodiments of the present technology. The assembly includes a portion of an arm 304 (or other portion of the cutting portion 300 and/or capture portion 200), a blade 302, and a coupler 1400. Any portion of the cutting portions 300 and capture portions 200 described herein can include one or more openings, such as openings 324 shown extending through arm 304. The openings 324 can be configured to receive a corresponding tab 320 extending from the blade 302 in a direction away from the sharpened edge of the blade 302. The tabs 320 can have one or more openings 322 configured to receive a corresponding protrusion 1302 positioned along the coupler 1400. The tabs 320 on the blades 302 are positioned through the openings 324 on the arm 304 such that the openings 322 on the tabs 320 are exposed on the non-receiving side of the arm openings 324. The protrusions 1302a, 1302b, and 1302c on the coupler 1400 are then positioned through the tab openings 322, thereby locking the blade 302 onto the arm 304. The protrusions 1302 may also include features which allow the width of the protrusion to be increased and locked after insertion through slots 324, to further secure coupler 1400 and blade 302 to arm 304, as illustrated in the end protrusions 1302a and 1302b.

Figures 20A, 20B:
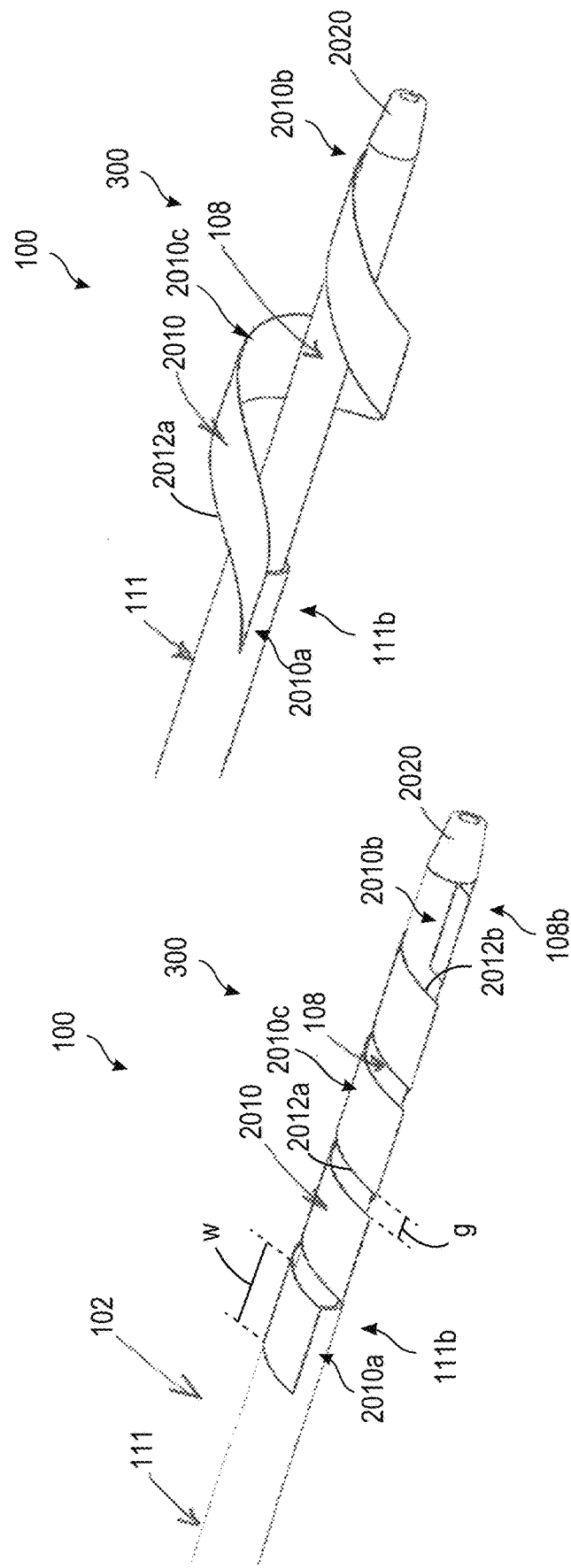
FIGS. 20A and 20B are perspective views of a treatment assembly configured in accordance with several embodiments of the present technology, shown in a collapsed state and an expanded state, respectively.

In some embodiments, as shown in FIGS. 20A and 20B, the treatment assembly 100 includes an elongated shaft 102 comprising first and second elongated members 111, 108 and a cutting portion 300 comprising a cutting element 2010 that extends helically and/or spirally around the longitudinal axis of the elongated shaft 102. The second elongated member 108 can be configured to be positioned within a lumen of the first elongated member 111 and extends distally beyond a distal terminus of the first elongated member 111. In some embodiments the axial positions of the first and second elongated members 111, 108 are fixed, and in some embodiments the first and second elongated members 111, 108 are slidably disposed relative to one another. In any case, the first and second elongated members 111, 108 may be configured to rotate relative to one another. The treatment assembly 100 may optionally include a tapered distal tip 2020 at the distal end portion 108b of the second elongated member 108.

The cutting element 2010 can have a proximal end portion 2010a at a distal end portion 111b of the first elongated member 111, a distal end portion 2010b at a distal end portion 108b of the second elongated member 108, and an intermediate portion 2010c extending between the proximal and distal end portions 2010a, 2010b. The intermediate portion 2010c wraps around the longitudinal axis of the treatment assembly 100. The cutting element 2010 is transformable between a collapsed configuration (FIG. 20A) and an expanded configuration (FIG. 20B). In the collapsed configuration, the cutting element 2010 is wound around the second elongated member 108 and has an outer diameter slightly larger than that of the second elongated member 108. The cutting element 2010 may wrap around the longitudinal axis less than one turn (360 degrees) or more than one turn (including multiple turns). When the second elongated member 108 is rotated with respect to the first elongated member 111 (or vice versa) in a first direction, the cutting element 2010 unwinds and expands radially outwardly, as shown in FIG. 20B. Rotation of the second elongated member 108 with respect to the first elongated member 111 (or vice versa) in a second direction opposite the first direction forces the cutting element 2010 to wind down onto the second elongated member 108, thereby radially collapsing the cutting element 2010. The amount of rotation controls the amount of expansion, with the actual expansion percentage depending on, for example, the initial diameter of the elongated shaft 102 and the length of the cutting element 2010.

In some embodiments, the cutting element 2010 comprises a ribbon having a width w (labeled in FIG. 20A) and longitudinal sides 2012a, 2012b (referred to collectively as "longitudinal sides 2012"). The width can be constant along the length of the ribbon or may vary. One of the longitudinal sides 2012 can be proximally facing 2012a and one of the longitudinal sides can be distally facing 2012b. The ribbon can be made from, for example, one or more resilient and/or superelastic metals or polymers. One or both longitudinal sides 2012 of the ribbon may be configured to cut obstructive material in a vessel lumen. For example, in some embodiments one or both longitudinal sides 2012 of the ribbon are sharpened. Additionally or alternatively, one or both longitudinal sides 2012 of the ribbon may be serrated. One or both longitudinal sides 2010 may have both serrated and sharpened portions to enhance the cutting ability of the cutting element 2010 when moved (e.g., rotated and/or translated) through obstructive material. In some cases it may be beneficial to have the proximally facing longitudinal side 2012a sharpened and/or serrated and the distally facing longitudinal side 2012b atraumatic and/or rounded. This configuration enables the device to cut through obstructive material when pulled and/or rotated in a proximal direction while reducing the risk of trauma to the vessel wall during advancement of the treatment assembly 100 to a treatment site. According to several embodiments, only the portion of the proximally facing longitudinal side 2012a that is proximal of the maximum diameter of the cutting element 2010 (when the cutting element 2010 is in an expanded state) is configured to cut through obstructive material. This configuration can reduce trauma to the native vessel wall as the treatment assembly 100 is pulled proximally and/or rotated through a treatment site.

Once the cutting element 2010 is expanded, the treatment assembly 100 can be rotated, translated, or both in order to cut obstructive material. In some embodiments, expansion of the cutting element 2010 can cut obstructive material. The cutting element 2010 can be repeatedly expanded and collapsed to engage and cut obstructive material. Movement of the cutting element 2010 to cut obstructive material may be performed manually by the user, facilitated by actuators on handle 12, or performed automatically with motors on handle 12.

Figure 21B:
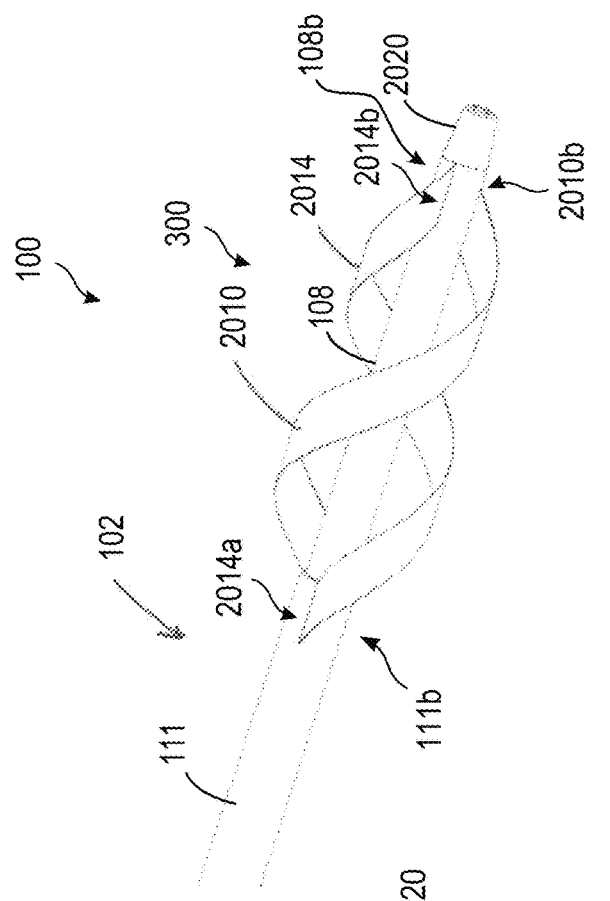
FIGS. 21A and 21B are perspective views of a treatment assembly configured in accordance with several embodiments of the present technology, shown in a collapsed state and an expanded state, respectively.
Figure 21A:
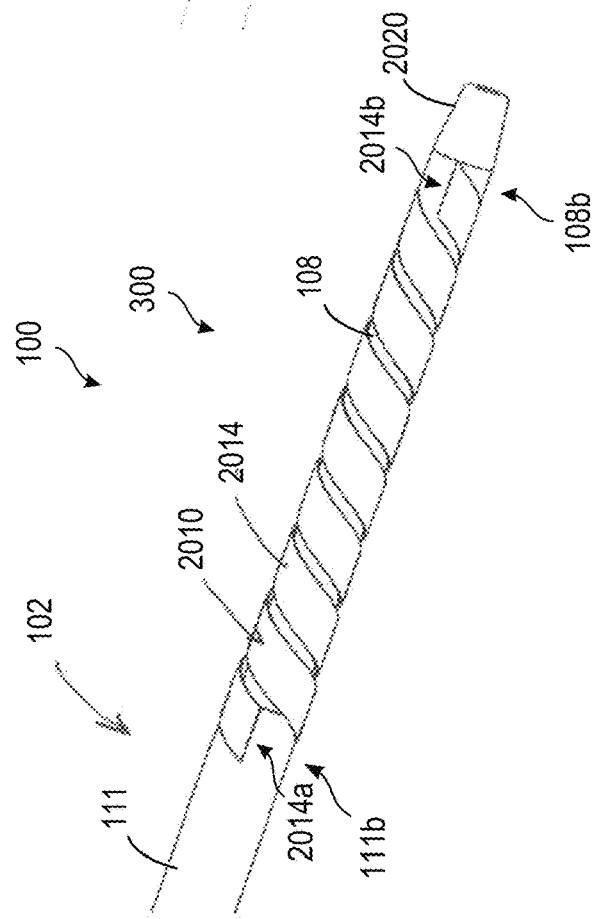

While only a single cutting element 2010 is shown in FIGS. 20A and 20B, the present technology includes treatment assemblies comprising more than one wrapped cutting element (e.g., two wrapped cutting elements, three wrapped cutting elements, four wrapped cutting elements, etc.). As but one example, FIGS. 21A and 21B show a treatment assembly 100 having first and second cutting elements 2010 and 2014. The treatment assembly 100 is shown in a collapsed state in FIG. 21A and an expanded state in FIG. 21B. Each of the cutting elements 2010, 2014 has a proximal end portion 2010a, 2014a, respectively (2010a not visible in FIGS. 21A and 21B), disposed at the distal end portion 111b of the first elongated member 111, and a distal end portion 2010b, 2014b, respectively, disposed at the distal end portion 108b of the second elongated member 108. The proximal end portions 2010a, 2014a can be coupled to the first elongated member 111 at different circumferential locations that are spaced apart about the circumference of the first elongated member 111. Whether two or more than two cutting elements are utilized, the spacing may be the same between adjacent cutting elements 2010 or may be different. In some embodiments, the proximal end portions 2010a, 2014a are coupled to the first elongated member 111 at diametrically opposed locations. In other embodiments, the proximal end portions 2010a, 2014a have other circumferential spacings. Likewise, the distal end portions 2010b, 2014b can be coupled to the second elongated member 108 at different circumferential locations that are spaced apart about the circumference of the second elongated member 108. The spacing may be the same between adjacent cutting elements 2010 or may be different. In some embodiments, the distal end portions 2010b, 2014b are coupled to the second elongated member 108 at diametrically opposed locations. In other embodiments, the distal end portions 2010b, 2014b have other circumferential spacings. In those embodiments having two or more cutting elements 2010, the different cutting elements 2010 can have the same or different widths.

The diameter of the elongated shaft 102 (and/or one or more components thereof), the number of cutting elements 2010, the angle at which the cutting element 2010 couples to the elongated shaft 102 (and/or one or more components thereof), the number of windings, and the width of the cutting element 2010 may be varied to create a desired expanded cutting configuration. As used herein with respect to the wrapped cutting elements, "length" is measured along the longitudinal axis of the cutting element 2010 which extends through a cross-section of the cutting element 2010. In some embodiments, the elongated shaft 102 is 3 mm in diameter, the length of the cutting element 2010 is 22 mm, the width of the cutting element 2010 is 2 mm, and the cutting element 2010 is coupled to the elongated shaft 102 at an angle of 60 degrees. In the collapsed state, the cutting element 2010 can be tightly wound around the elongated shaft 102 two times. In the expanded state (e.g., after rotation of the second elongated member 108), the cutting element 2010 is unwound until it makes only one turn around the elongated shaft 102, which approximately doubles the maximum diameter of the cutting element 2010 (in this case, to about 6 mm). According to some embodiments, the cutting element 2010 is coupled to the elongated shaft 102 at an angle of 60 degrees, is 33 mm long and wound around the elongated shaft 102 approximately three times. In the expanded state, the cutting element 2010 is unwound until it makes one turn around the elongated shaft 102, which approximately triples the maximum diameter of the cutting element 2010 (in this case, about 9 mm). In some embodiments, the cutting element 2010 has a length of 40 mm, is coupled to the elongated shaft 102 at an angle of 45 degrees, and is wound around the elongated shaft 102 approximately three times. In certain embodiments, the cutting element 2010 has a length of 57 mm, is coupled to the elongated shaft 102 at an angle of 30 degrees, and is wound around the elongated shaft 102 approximately 3 times. In the latter two examples, the cutting element 2010 can be unwound to its fully expanded diameter in which it has one turn and a diameter that is about 3 times its starting diameter (e.g., around 9 mm). However, because the attachment angle is less acute (as compared to the earlier examples), but over a longer length due to the less acute attachment angle. For example, at the 60 degree attachment angle, the helix length is about 16 mm, for the 45 degree attachment angle, the helix length is about 28 mm, and for the 30 degree attachment length the helix length is 49 mm, all over 3 windings.

The fully expanded diameter of the cutting element 2010 also depends on the design of the attachment of the proximal and distal end portions 2010a, 2010b of the cutting element 2010 to the first and second elongated members 111, 108, respectively, of the elongated shaft 102. For example, if an end of the cutting element 2010 were fixedly welded or soldered to the corresponding first or second elongated member 111, 108, the cutting element 2010 would remain tangent or near tangent to the elongated shaft 102 as it was unwound, creating one slope angle of helical taper on each end of the cutting element 2010. Whereas, if the cutting element 2010 were allowed to angle away from the elongated shaft 102 to a certain degree or was freely allowed to hinge at the elongated shaft 102, the helical taper would be another slope angle. Each type of helical taper would alter the fully unwound diameter to some extent.

In some embodiments, the width of the cutting element 2010 can be selected based on a desired gap length g (see FIG. 20A) between windings when the cutting element 2010 is fully wound (e.g., in a collapsed state). Additionally or alternatively, the width w (see FIG. 20A) of the cutting element 2010 can depend on how many cutting elements 2010 there are in the treatment assembly 100. If the treatment assembly 100 has more than one, the width of the individual cutting elements 2010 will be less than if only a single cutting element 2010 were used. The greater the width w of a given cutting element 2010, the more resistance it will have to bending distortion when under load, and the more effectively it can cut obstructive material. As demonstrated, there are trade-offs between the number of cutting elements 2010 and performance of each cutting element 2010.

As discussed, the second elongated member 108 may rotate with respect to the first elongated member 111 when expanding the treatment assembly 100, and in some embodiments the second elongated member 108 may also translate with respect to the first elongated member 111 to axially compress or elongate the cutting element 2010. The ability of the cutting element 2010 to be axially compressed or elongated depends in part on how the proximal and distal end portions 2010a, 2010b of the cutting element 2010 are coupled to the first and second elongated members 111, 108 of the elongated shaft 102, and whether the attachment enables the attachment angle to vary, as axial compression or elongation of the cutting element 2010 increases or decreases the angle of attachment. The ability to axially compress and elongate the cutting element 2010 while in the expanded state improves the cutting efficiency of the treatment assembly 100. For example, the treatment assembly 100 may separate and capture obstructive material from a combination of one or more expanded wrapped cutting elements rotating, translating, expanding, and/or compressing through obstructive material of a treatment site. Additionally, the cutting element 2010 may be partially unwound for a first cutting pass, and then further unwound to a more expanded and/or fully expanded state for a second cutting pass, and so forth for multiple cutting passes until the desired effect is achieved.

In some variations, the cutting element 2010 is integral to the first elongated member 111. For example, the first elongated member 111 can comprise a tubular member that has been cut in a helical and/or spiral pattern at its distal portion to create one or more helical strips. As such, the first elongated member 111 and the cutting element 2010 can comprise the same material. The distal end portion 2010b of the cutting element 2010/distal end portion 111b of the first elongated member 111 can be fixed to the distal end portion 108b of the second elongated member 108. When the second elongated member 108 is rotated with respect to the first elongated member 111, the cut strip (now the cutting element 2010) is unwound and expands outward. The foregoing embodiments advantageously do not require any attachment design and therefore reduce the number of manufacturing processes.

In another variation, the cutting element 2010 is formed from one material that has the required mechanical properties including the ability to be wound and unwound, sharpened, and hold sufficient rigidity to have an effective cutting action when manipulated as described above, and the first elongated member 111 is formed from a separate tube. The first elongated member 111 is then attached to a second tube that extends proximally from the treatment assembly 100 and that has suitable properties for a catheter shaft component, for example cost, flexibility, etc.

There are many possible methods to attach the proximal end portion 2010a of the cutting element 2010 to the first elongated member 111 and the distal end portion 2010b to the second elongated member 108, for example via soldering, welding, gluing, mechanical attachment, or some combination thereof. As noted above, the method of attachment can affect the specific expansion performance and strength of attachment of the cutting element 2010 when it is expanded and used to remove obstructive material.

In some embodiments, for example as shown in FIGS. 22A, 22B, and 22C, the distal end portion 2010b of the cutting element 2010 is mechanically captured between the distal end portion of the second elongated member 108 and a securing element 2220. The distal end portion 2010b of the cutting element 2010 can be coupled to a cylindrical coupler 2210 (e.g., a dowel, a tube, or other cylindrical component) and extend from the coupler 2210 at an angle. The angle between the coupler 2210 and the cutting element 2010 forms the angle at which the cutting element 2010 extends from the second elongated member 108. In some embodiments, the coupler 2210 is integral with the cutting element 2010. For example, the coupler 2210 can be constructed by rolling the cutting element 2010 into a tight cylinder at the distal end portion 2010b. In some embodiments, the coupler 2210 is a separate component that is attached to the distal end portion 2010b of the cutting element 2010. In any case, the coupler 2210 can be configured to be received within a groove 2230 extending along a distal portion of the second elongated member 108. The securing element 2220 can be a band that is configured to be slidably disposed over the outer surface of the second elongated member 108. The securing element 2220 can have a slot 2225 extending along less than its entire length. The slot 2225 can be continuous with an opening at a distal end of the securing element 2220.

As shown in FIG. 22B, the cutting element 2010 can be mechanically captured at the distal end portion of the second elongated member 108 by inserting the coupler 2210 into the groove 2230 in the second elongated member 108, and sliding the securing element 2220 upward to capture the coupler 2210 within the slot 2225. The slot 2225 in the securing element 2220 can be wide enough to allow the cutting element 2010 to extend radially outwardly therethrough, but too narrow to allow passage of the coupler 2210. The coupler 2210 is configured to rotate within the groove 2230, thereby allowing the extension angle of the cutting element 2010 (relative to the second elongated member 108) to vary. The width of the slot 2225 may be varied to allow a varied range of motion of the coupler 2210 (and thus the cutting element 2010) in the groove 2230 when the treatment assembly 100 is expanded. In FIG. 22C the groove 2230 is shown extending proximally beyond the securing element 2220, but in other embodiments the groove 2230 may terminate at more distal locations (including aligned with or distal to a proximal terminus of the securing element 2220). In some embodiments, the coupler 2210 is fixed within the groove 2230 such that it cannot rotate relative to the second elongated member 108.

The second elongated member 108 can have a tapered distal tip 2020 at its distal end. The tapered distal tip 2020 is removed from view in FIG. 22B to show the coupler 2210 in the groove 2230, but shown in FIG. 22C to illustrate how the coupler 2210 and cutting element 2010 are mechanically captured. The distal tip 2020 can prevent distal axial movement of the securing element 2220 and the coupler 2210, thereby securing the coupler 2210 within the slot 2225 in the securing element 2220. In some embodiments, the distal tip 2020 has a maximum diameter that is greater than the diameter of the second elongated member 108. In some embodiments, the coupler 2210 is secured within the slot 2225 via other means, such as a non-tapered distal cap, tube, or other component to prevent securing element from sliding out of the slot 2225. In these and any embodiments disclosed herein, the second elongated member 108 can have a lumen 22 extending therethrough. The distal tip 2020 can also include a lumen that is an extension of lumen 22.

The securing element 2220 and/or second elongated member 108 can include one or more securing means so that when the securing element 2220 is in position over the coupler 2210, the axial and rotational position of the securing element 2220 (and thus axial position of the coupler 2210) is fixed relative to the second elongated member 108. For example, the securing element 2220 may have one or more side holes (not shown) and the second elongated member 108 may have one or more protrusions that spring radially outwardly into the side holes when the side holes are aligned with the protrusions. In some embodiments, the securing element 2220 includes one or more tabs (not shown) which can be pushed radially inward to lock into one or more receptacles in the second elongated member 108. Additionally or alternatively, the securing element 2220 can be soldered, welded, or glued to the second elongated member 108 to hold the securing element 2220 in place.

The proximal end portion 2010a of the cutting element 2010 may be mechanically captured at a distal portion of the first elongated member 111. For example, the first elongated member 111 may include a groove similar to the slot 2225 on the securing element 2220. In such embodiments, the second elongated member 108 can have a recess in its outer surface so that the second elongated member 108 can rotate freely with respect to the first elongated member 111 to expand and collapse the cutting element(s) 2010. As previously mentioned, in some embodiments the cutting element 2010 is integral with and an extension of the first elongated member 111.

The coupler 2210 can have other shapes and configurations. For example, in some embodiments the distal end portion 2010b of the cutting element 2010 may be cut (e.g., laser cut) to have a T-shaped distal end that is configured to be received within the slit 2225 of the securing element 2220. The T-shaped distal end (or portion thereof) is then trapped in place between the securing element 2220 and the second elongated member 108. The treatment assembly 100 can include a distal tip to secure the T-shaped distal end in place.

In any of the embodiments including one or more cutting elements 2010, the treatment assembly 100 may optionally include an expandable member (e.g., a balloon) (not shown) disposed radially inwardly of the cutting element 2010. The expandable member can be configured to be expanded underneath the already-expanded (partially or completely) cutting element 2010 to add radial force to the cutting element 2010 and prevent or reduce distortion of the cutting element 2010 as the treatment assembly 100 is translated and/or rotated through the treatment site. The expandable member may be aligned with only the intermediate and/or distal portions of the cutting element 2010 (i.e., and not the proximal portion), so as not to interfere with the cutting action of the cutting element 2010 on the proximal aspect of the treatment assembly 100.

Figures 23A, 23B:
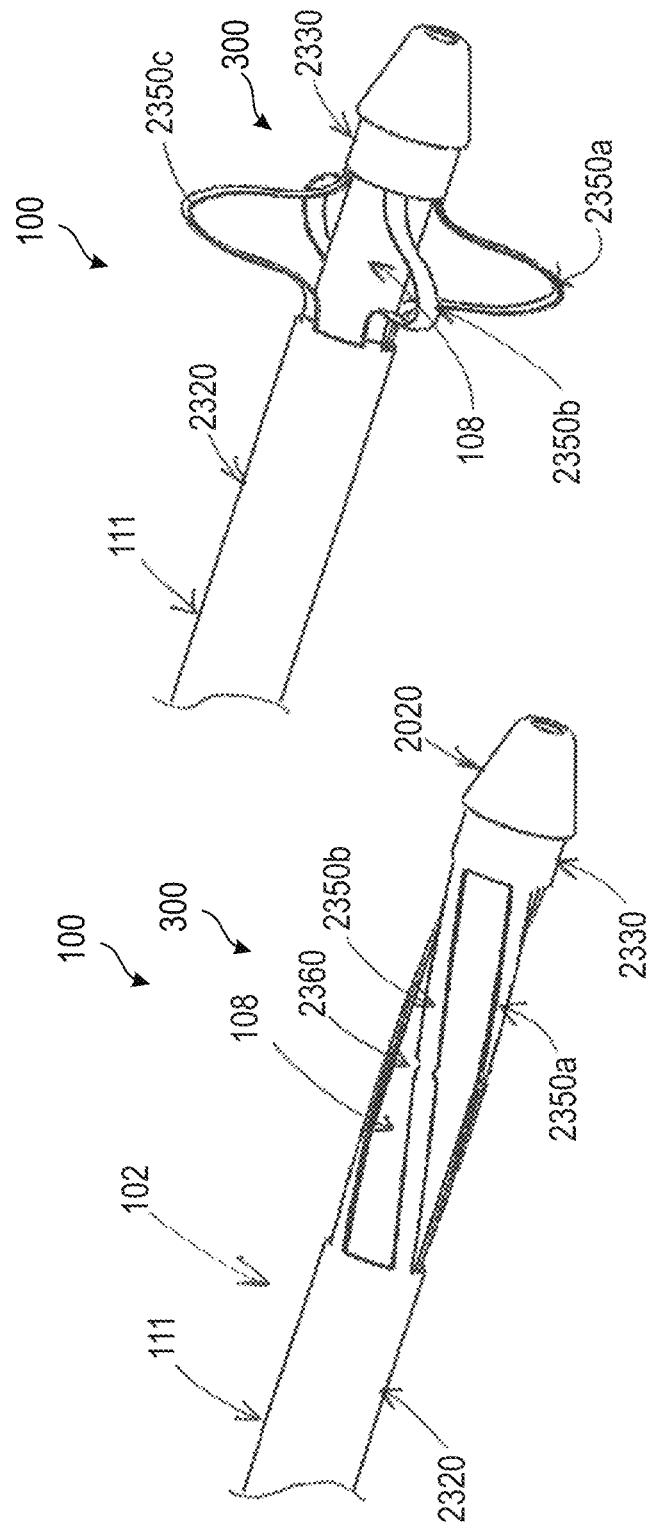
FIGS. 23A and 23B perspective views of a treatment assembly configured in accordance with several embodiments of the present technology, shown in a collapsed state and an expanded state, respectively.

In some embodiments, for example as shown in FIGS. 23A and 23B, the treatment device includes an elongated shaft 102 comprising first and second elongated members 111, 108 and a cutting portion 300. The first elongated member 111 comprises an elongated tube 2320, a distal band 2330, and two or more strips 2350 connecting the proximal tube 2320 to the distal band 2330. In a collapsed state, the strips 2350 may be parallel to the axis of the elongated shaft 102, or may be at a slight angle (e.g., between 0 and 20 degrees) from the axis of elongated shaft 102 (as shown in FIG. 23A). The second elongated member 108 can be configured to be slidably disposed within a lumen of the first elongated member 111. The second elongated member 2003 can extend through the proximal tube 2320 and the portion underlying the strips 2350, and distally beyond the distal band 2330. The treatment assembly 100 can comprise a distal tip 2020 coupled to the distal end of the second elongated member 2003 that has a maximum diameter larger than the diameter of the distal band 2330. In some embodiments, the distal tip 2020 is locked to the distal band 2330 of the first elongated member 111 by means of locking elements on the second elongated member 108 and distal band 2330. For example, the distal band 2330 can have side holes and the second elongated member 108 may have protrusions that spring outwards into the side holes. In some embodiments, the distal band 2330 has tabs which can be pushed radially inward to lock into receptacles in the second elongated member 108. Additionally or alternatively, the second elongated member 108 and distal band 2330 can be attached, for example, via welding, glue, or soldering.

In any case, when the second elongated member 108 is pulled proximally, the distance between the distal band 2330 and the distal end of the proximal tube 2320 shortens and the strips 2350 on the first elongated member 111 bow radially outwardly to form expanded arms, as shown in FIG. 23B. In those embodiments where the strips 2350 are attached to the first elongated member 111 at an angle (as shown in FIGS. 23A and 23B), the arms are somewhat twisted in the plane perpendicular to the elongated shaft 102. The strips 2350 might have one or more edges that are sharpened and/or serrated. When expanded, the treatment assembly 100 may be rotated and/or translated to act as rotary blades to remove obstructive material from the treatment site. The amount of expansion depends on the amount of translation of the second elongated member 108 relative to the first elongated member 111. In use, the arms may be partially extended outwards for a first pass, and then further expanded for a second pass, etc., to remove obstructive material more effectively.

Figure 24:
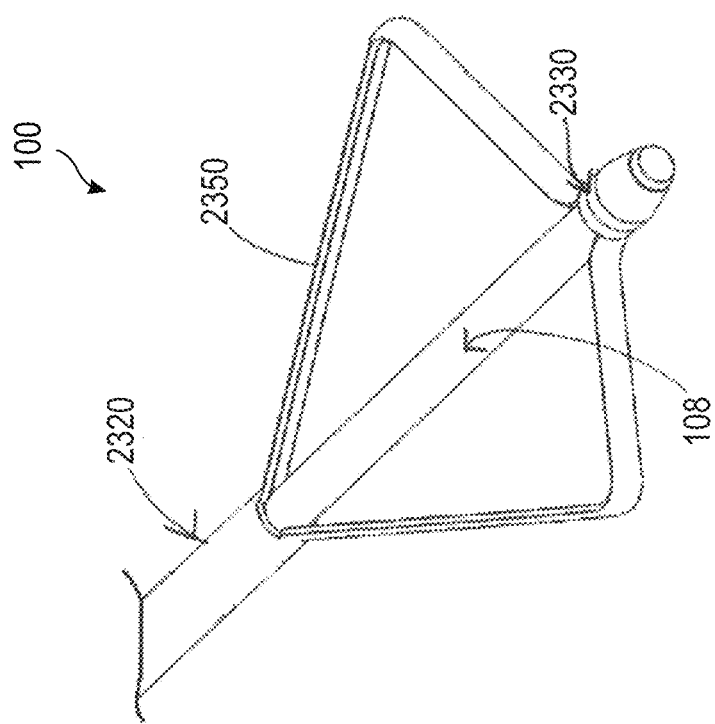
FIG. 24 is a perspective view of a treatment assembly configured in accordance with several embodiments of the present technology, shown in an expanded state.

The strips may be integral to the first elongated member 111. As seen in FIG. 23A, the first elongated member 111 can be cut (e.g., laser cut) to create one or more strips, parallel to or at a slight angle to the axis of the elongated shaft 102. Optionally the cut pattern includes recessed portions 2360 along the length of one, some, or all of the strips 2350 to urge the strip 2350 to preferentially bend at the recessed portions 2360. The recessed portions 2360 may be at the midpoint of the strip 2350, to create a symmetric expanded geometry, or may be biased towards the distal end of the strip 2350 to create an asymmetrical expanded geometry, as illustrated in FIG. 24. The latter configuration may allow for a better cutting angle of the strip cutting edge against the obstructive material.

Figure 25:
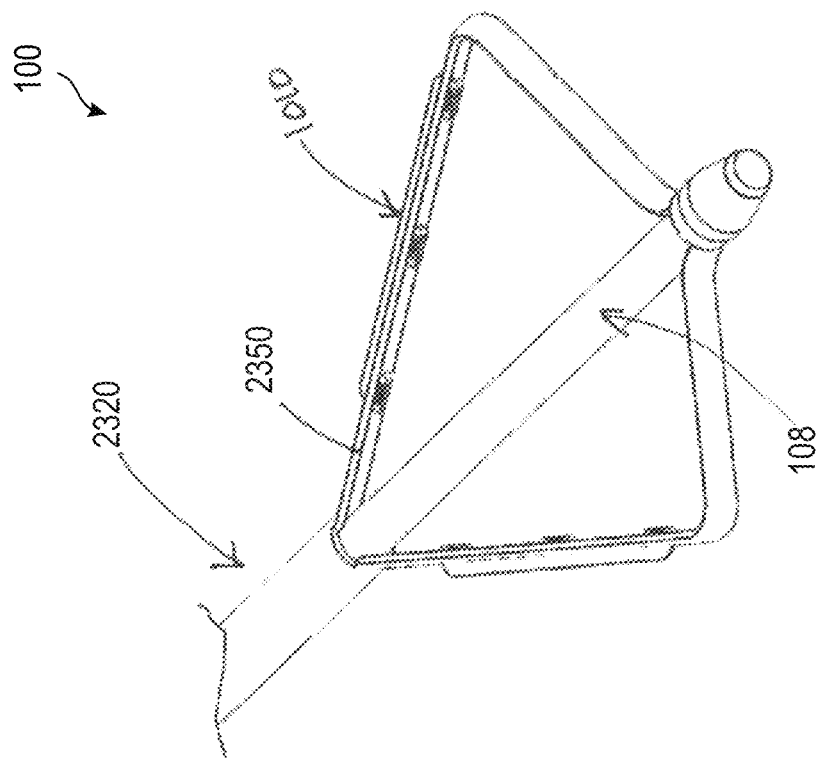
FIG. 25 is a perspective view of a treatment assembly configured in accordance with several embodiments of the present technology, shown in an expanded state.

In some embodiments, the strips 2350 are not the cutting element. Instead, as seen in FIG. 25, the strips 2350 contain tabs or other features that allow a second cutting element, such as a blade 1010, to be attached to each strip 2350. In this variation, the first elongated member 111 may be made from one material that is configured to be expanded and collapsed, and the blade 1010 may be made from a second material that is suited to have a sharpened blade edge. The blade 1010 may be secured to strips 2350 by means of a separate latch component (not shown). Additionally or alternatively, the blade 1010 may be soldered or welded to the strip 2350.

Figure 26:
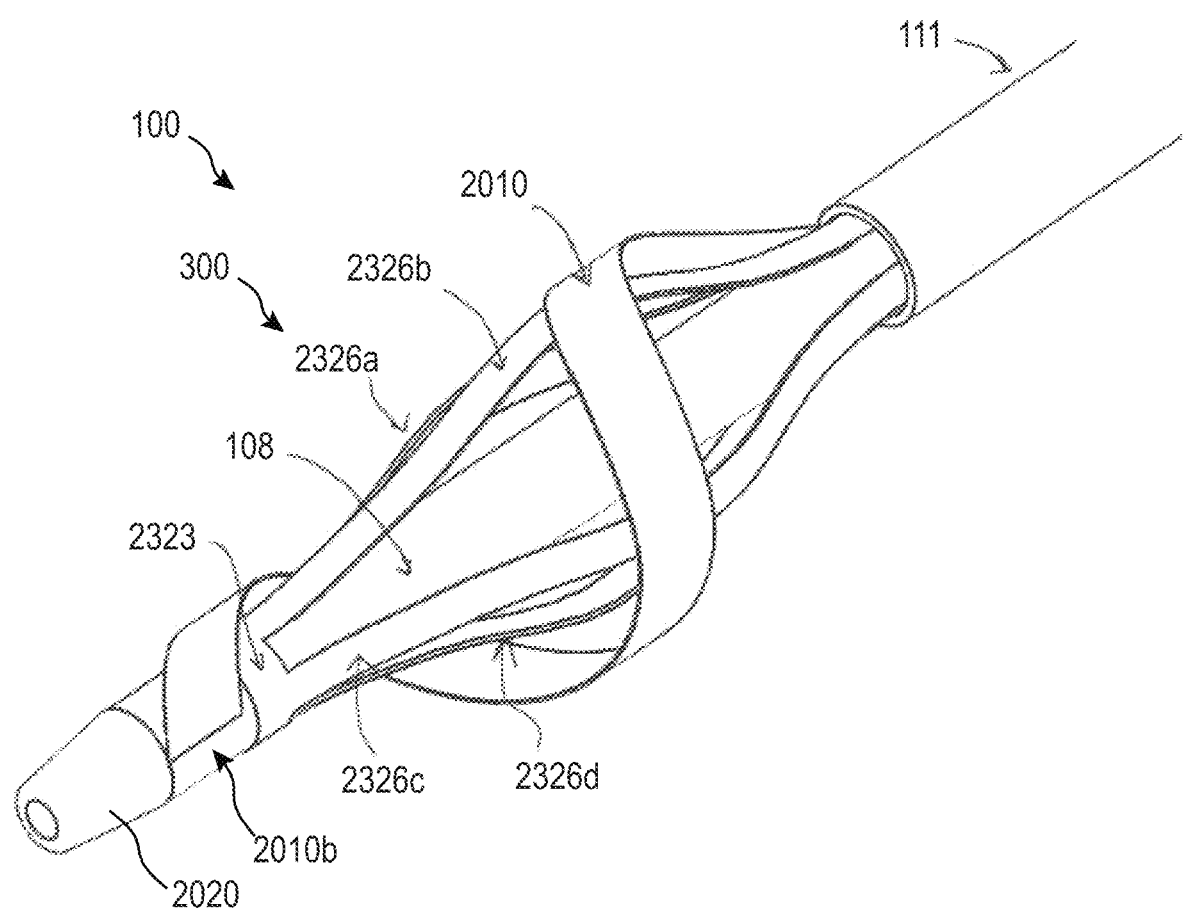
FIG. 26 is a perspective view of a treatment assembly configured in accordance with several embodiments of the present technology.

In some instances, it may be desirable to have an additional cutting element orientated in the opposite direction of the existing cutting element to provide a counter-force during cutting of obstructive material. For example, in some embodiments the device may include one or more inner cutting elements (such as cutting element 2010) positioned inside one or more outer cutting elements (such as cutting element 2010). The inner cutting elements can be substantially linear (for example as shown in FIG. 23) or may be helical and/or spiral (for example as shown in FIGS. 20A and 20B). The outer cutting elements can be substantially linear (for example as shown in FIG. 23) or may be helical and/or spiral (for example as shown in FIGS. 20A and 20B). In some embodiments, the device 101 may comprise an inner elongated member 108, an outer elongated member 111 with one or more cutting element(s) 2010, and an elongated member located between the inner and outer elongated members 108, 111 that comprises one or more cutting elements. In such embodiments, the cutting elements can be integral to the outer and intermediate elongated members, or may be separate elements attached to the outer and intermediate elongated members. The handle 12 of the device 101 (FIG. 1) may have an actuator that controls the rotational movement of the outer and middle elongated members. For example, an actuator(s) on the handle 12 may be configured to turn the outer elongated member 111 in one direction while either keeping the inner cutting element (carried by the intermediate elongated member) stationary or rotating the inner cutting element in the opposite direction. In some embodiments, for example as shown in FIG. 26, a cutting portion 300 of the treatment assembly 100 comprises an inner elongated member 108, an outer elongated member 111 with one or more attached or integral cutting elements 2010, and an intermediate member 2323 located between the inner elongated member 108 and the outer elongated member 111, with corresponding cutting elements 2326 (labeled individually in FIG. 26 as 2326a-2326d). In such embodiments, the handle 12 (FIG. 1) can include one or more actuators to rotate the outer elongated member 111 in one direction with respect to the inner elongated member 108 while shortening the intermediate elongated member 2323 to expand the cutting elements 2326 radially outwardly during deployment. The handle 12 can be configured to further actuate the outer and intermediate elongated members 111, 2326 to rotate and/or translate to cut the obstructive material. One, some, or all of the cutting elements 2010 can have a sharpened edge, and one, some, or all of the cutting elements 2326 can have a sharpened edge. In some embodiments, only the outer cutting elements 2010 or only the inner cutting elements 2326 may have a sharpened edge. In those embodiments including inner and outer cutting element(s) with sharpened edges, the sharpened edges can be configured to face each other. As such, the inner and outer cutting elements 2326, 2010 can be configured to trap obstructive material as they move towards one another to cut the obstructive material. The inner and outer cutting elements 2326, 2010 can thus provide a counterforce to the cutting force (or any force) exerted on the obstructive material by the other.

In a similar fashion, the embodiment shown in FIGS. 23A and 23B could have one or more expandable cutting elements located inside the outer cutting elements. The treatment assembly 100 can have an intermediate elongated member located between the inner elongated member 108 and the outer elongated member 111, with corresponding expandable cutting elements. The inner and outer cutting elements could be configured such that when expanded, the cutting edges of the inner cutting elements are canted in one direction and the cutting edges of the outer cutting elements are canted in the opposite direction. As above, the handle 12 can have an actuator that controls the rotational movement of the outer and intermediate elongated members. For example, the handle 12 may be configured to turn the outer elongated member 111 in one direction while either keeping the intermediate member stationary or rotating the intermediate member in the opposite direction.

Figure 27A:
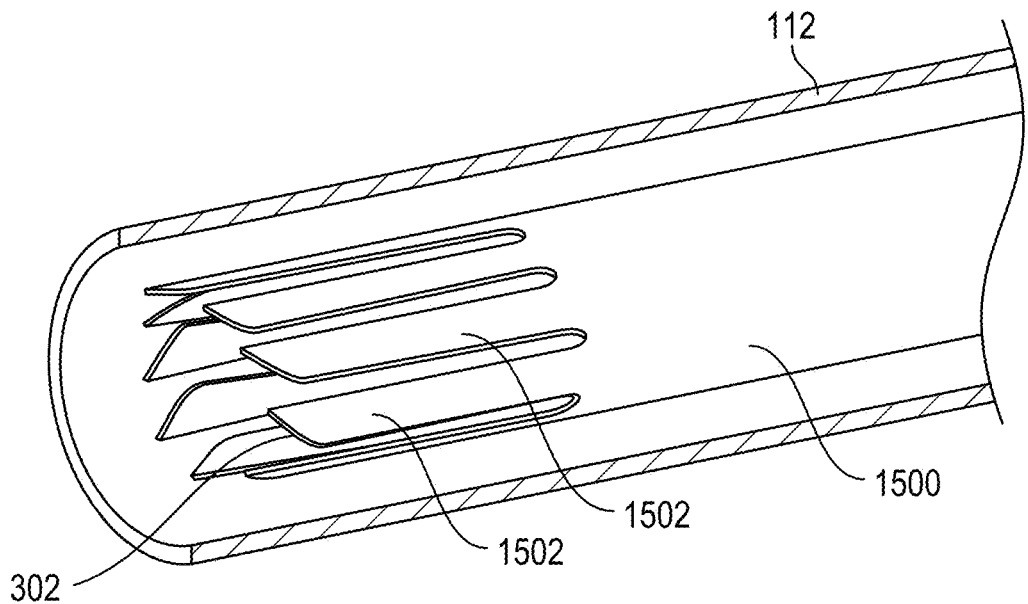
FIGS. 27A and 27B are isometric views of a cutting portion configured in accordance with several embodiments of the present technology.
Figure 27B:
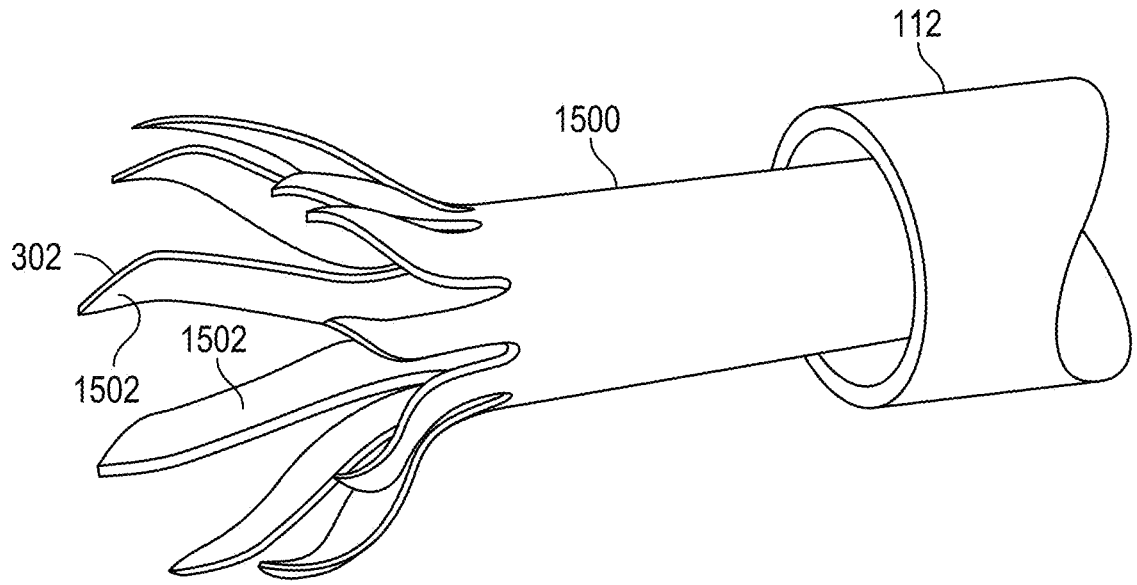
Figure 27C:
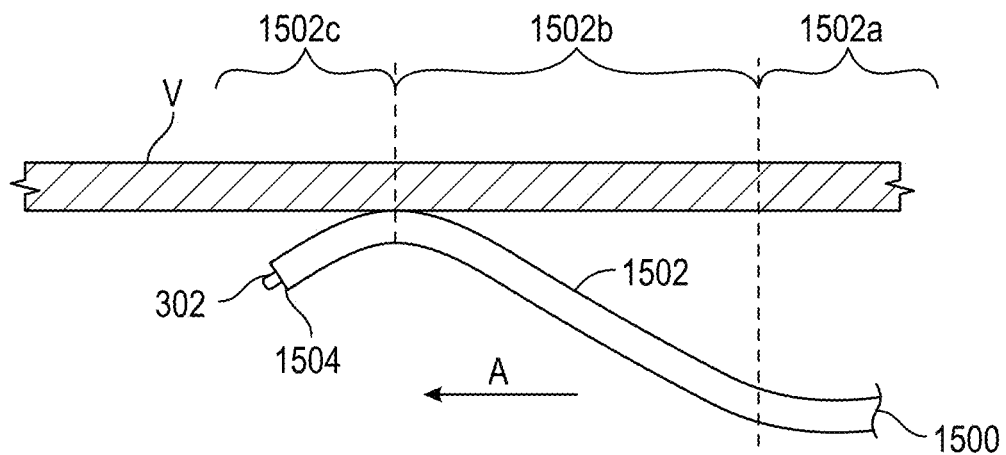
FIGS. 27C and 27D are side views of an arm of the cutting portion shown in FIGS. 27A and 27B, shown isolated from the treatment assembly and configured in accordance with several embodiments of the present technology.
Figure 27D:
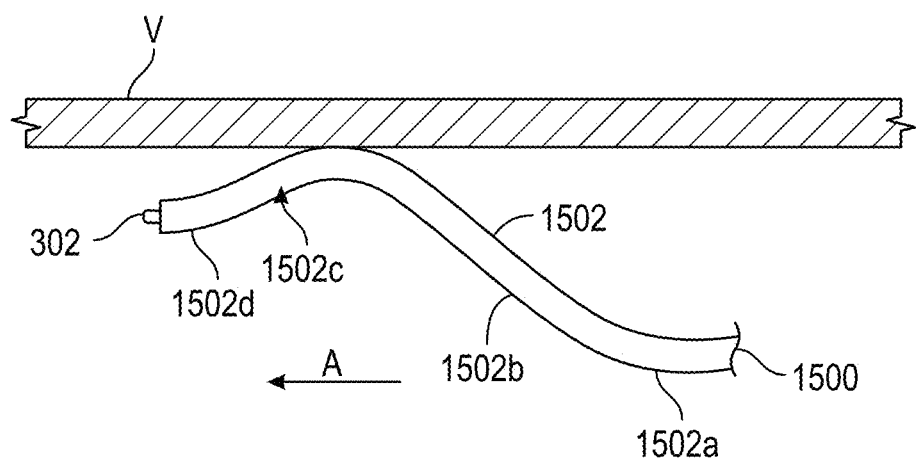

In some embodiments, the cutting portion 300 can be configured as provided in FIGS. 27A-27D. In such embodiments, the cutting portion 300 can be made from a superelastic tube such as nitinol or others, with a cut pattern than forms multiple (2 or more) arms 1502 protruding from the distal end of the nitinol tube. The arms 1502 can be heat-set to expand outward in a larger diameter than the base tube once a sleeve 112 is retracted. One, some, or all of the arms 1502 can be shape set to assume the shape shown in the side views of FIGS. 27C and 27D. As shown in FIG. 27C, the arm 1502 can have a first substantially linear portion 1502a extending from the tube, a second portion 1502b extending distally and radially outwardly from the first portion 1502a, and a third, distal-most portion 1502c extending distally and radially inwardly from the second portion 1502b. The curve between the second and third portions 1502b, 1502c forms an atraumatic surface that can slide along the vessel wall. In such embodiments, the cutting element 302 can project distally from the distal terminus 1504 of the arm 1502 and along a dimension that is substantially parallel to the vessel axis and along the direction of movement of the arm 1502 (indicated by arrow A). In some embodiments, for example as represented by FIG. 27D, one, some, or all of the arms 1502 include a fourth portion 1502d extending distally from the third portion 1502c along a dimension that is substantially parallel to the vessel axis and along the direction of movement of the arm 1502 (indicated by arrow A).

One, some, or all of the arms 1502 can have a beveled and sharpened point. Like the cutting portion 300 in FIGS. 8-9B, the cutting portions in the embodiments represented by FIGS. 27A-27D form a circumferential pattern, although since the blades do not overlap in the collapsed configuration, the cuts will not be as close together. However, because they are not required to overlap in the collapsed configuration, the collapsed profile takes up less space, which can be advantageous for an endovascular device.

Figure 28A:
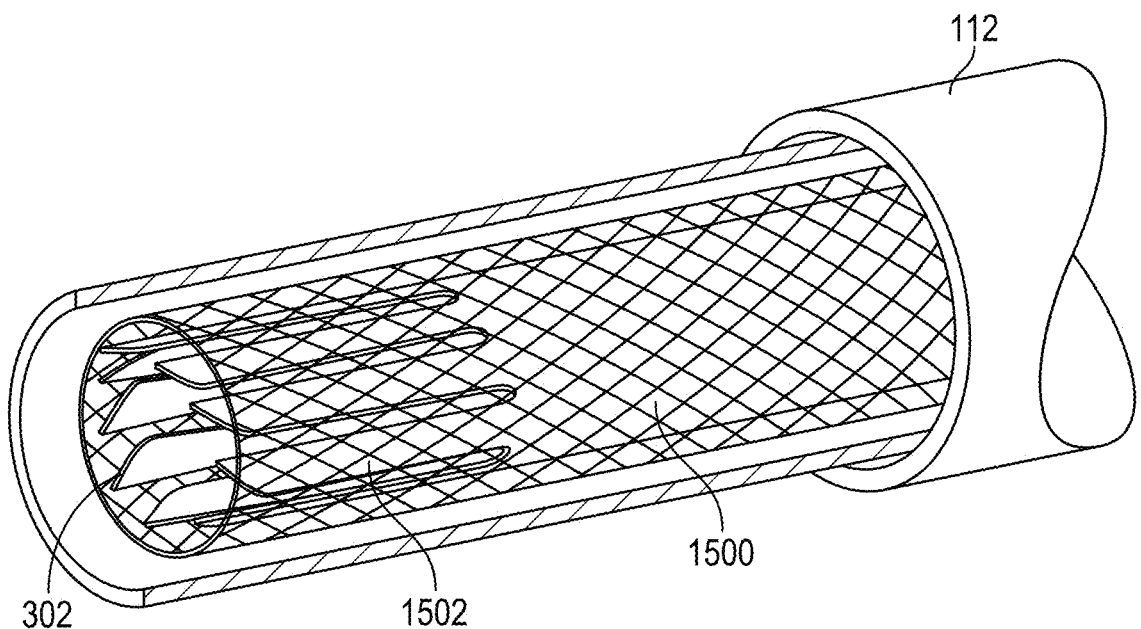
FIGS. 28A and 28B are isometric views of a cutting portion configured in accordance with several embodiments of the present technology.
Figure 28B:
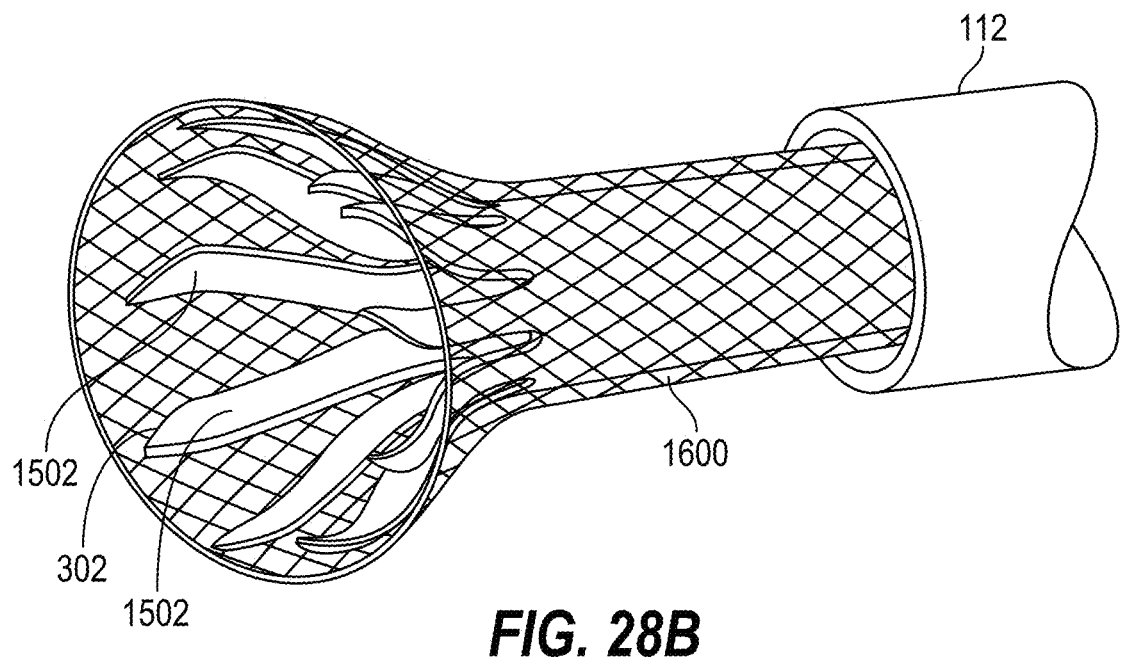

FIGS. 28A and 28B are isometric views of a cutting portion configured in accordance with several embodiments of the present technology. FIG. 28A shows the cutting portion in a collapsed state. FIG. 28B shows the cutting portion in an expanded state. The system 10 and/or assembly 100 of FIGS. 28A and 28B can be generally similar to the system 10 and/or assembly 100 of FIGS. 27A-27D, except in FIGS. 28A and 28B, the system 10 includes a cover 1600 positioned over all or a portion of the cutting portion 300. The cover 1600 can be a braid, a weave, a fabric, a polymer material, etc.

C. Example Methods of Use

Various approaches may be used to gain intravascular access to the obstructive material within the vessel lumen. In some embodiments, the method includes percutaneously accessing the blood vessel lumen (such as a vein) with a guidewire, advancing the introducer sheath (such as any of the introducers disclosed herein) over the guidewire and through the access site, and inserting a treatment device (such as any of the treatment devices disclosed herein) through a lumen of the introducer sheath into the blood vessel lumen. The distal portion of the treatment device containing the treatment assembly can be advanced to a target treatment site within the vessel lumen. The access site can be at, for example, a femoral vein, an internal jugular vein, or a popliteal vein. In some embodiments the method includes aspirating or infusing a thrombolytic agent into or from the blood vessel before, during, or after extraction of the obstructive material.

In some embodiments, a guidewire may first be inserted into the blood vessel lumen and advanced through the obstructive material such that a distal terminus of the guidewire is distal of the obstructive material. Next, the introducer 103 (FIG. 1) may be delivered over the guidewire so that a distal portion of the introducer 103 (FIG. 1) is positioned within the vessel lumen proximal of the obstructive material. In those introducer 103 embodiments which include a funnel at the distal end of sheath 110, the funnel 700 be expanded into apposition with the blood vessel wall. The method can continue by inserting the treatment device 101 over the guidewire, through the introducer 103, and into the vessel lumen. In some embodiments, the treatment device 101 can be advanced through the obstructive material such that some or all of the treatment assembly 100 of the treatment device 101 is distal of the obstructive material. In some embodiments, the treatment assembly 100 can be advanced to a location in the vessel such that some or all of the treatment assembly 100 is proximal of the obstructive material.

According to some embodiments, the treatment assembly 100 may be contained within the sleeve 112 during delivery. Once the distal portion of the treatment device 101 is positioned at a desired location relative to the obstructive material at the treatment site, the sleeve 112 of the device 101 can be pulled proximally relative to the treatment assembly 100 (or the treatment assembly pushed distally relative to the sleeve 112) to release one or both of the cutting and capture portions of the treatment assembly 100, thereby allowing the capture portion 200 and/or cutting portion 300 to self-expand. In some embodiments, the treatment assembly 100 may be expanded distal of the obstructive material such that no portion of the capture portion 200 and no portion of the cutting portion 300 engages the obstructive material during and/or immediately after expansion. In some embodiments, at least a portion of one or both of the capture portion 200 and the cutting portion 300 self-expand within the obstructive material. In some embodiments, the capture portion 200 is distal to the obstructive material and the cutting portion 300 is proximal to the obstructive material. As described elsewhere herein, in some embodiments one or both of the capture portion 200 and the cutting portion 300 are not self-expanding and require mechanical actuation.

While the capture and cutting portions 200, 300 are in an expanded configuration, the cutting portion 300 can be pushed towards the capture portion 200 and/or the capture portion 200 can be pulled distally towards the cutting portion 300 (either serially, simultaneously or back and forth). Alternately, the capture and cutting portions 200 and 300 can be pulled in a proximal direction to simultaneously or serially cut and capture the obstructive material. Before, during, or after such movement, the entire treatment assembly 100 can be pushed distally or pulled proximally towards the sheath 110. As the assembly 100 and/or device 101 is pulled proximally, the blades 302 of the cutting portion 300 cut through the obstructive material in a direction generally parallel to the longitudinal axis of the blood vessel, thereby separating the obstructive material from the vessel wall and/or other obstructive material. The capture portion 200 collects the separated obstructive material and is then pulled into the sheath 110 for removal from the patient. As previously mentioned, in some embodiments the system 10 does not include an introducer sheath. In embodiments with a funnel 700 on the distal end of sheath 110, the funnel helps to capture all the obstructive material as the treatment device is pulled into the sheath and from them out of the of the blood vessel. In embodiments with aspiration capabilities, aspiration can be applied to one, some or all of the elongated shafts associated with the treatment system (e.g., the sheath 110, the sleeve 112, the outer member 111, etc.) to reduce the chance of embolic complications.

As previously mentioned, both the capture portion and the cutting portion may be self-expanding, so that when the sheath is retracted, the capture and cutting portions self-expand into the expanded state. Additionally or alternatively, the capture portion and/or the cutting portion may be expanded by active actuation. For example, one or both of the capture portion 200 and the cutting portion 300 may be coupled to an actuation member that, when actuated by the operator (via a handle at a proximal portion of the treatment device 101), causes the capture portion 200 and/or the cutting portion 300 to partially or fully expand. For example, in some embodiments the treatment device includes an actuation member that is coupled to a distal end region of a corresponding one of the capture portion 200 or cutting portion 300 and when pulled, shortens the length of that component which has the effect of expanding that component. In those embodiments where the capture portion 200 and the cutting portion 300 are integrated within a single expandable component, a single actuation member may cause both to expand and/or collapse together. Likewise, in those embodiments where the capture portion 200 and the cutting portion 300 are separate components, a single actuation member may cause both to expand and/or collapse together. In some embodiments where the capture portion 200 and the cutting portion 300 are separate components, each of the capture portion 200 and the cutting portion 300 may be independently actuatable, whether by separate actuation members or by different mechanisms or timings via the same actuation member.

According to various embodiments, one of the capture portion 200 or the cutting portion 300 is self-expanding and the other of the capture portion 200 or the cutting portion 300 requires active expansion. For example, the capture portion 200 can self-expand when the sheath is retracted, while the cutting portion 300 requires expansion with an actuation member. In this example, the cutting portion 300 may be expanded for only the first portion of the thrombus removal step to facilitate initial removal of the thrombus from the wall, but is then retracted during the remainder of the thrombus removal step as it is no longer needed.

According to several embodiments, the treatment assembly 100 of the treatment device 101 is positioned distal to the obstructive material, expanded, and then manipulated such as rotated, translated, or both, to separate obstructive material from the wall. For example, the treatment assembly can comprise one or more cutting elements (FIGS. 20A, 20B, 21A, etc.), and the inner elongated member is rotated to expand the cutting element to some or all of its expansion amount, and then manipulated to separate obstructive material from the treatment site. The treatment device can be readvanced for a further expansion and manipulation, in some cases to a larger expansion amount, for additional separation of obstructive material.

At any point before, during, or after the foregoing methods, aspiration may be applied at the treatment site to further reduce the risk of embolization.

At any point before, during, or after the foregoing methods, the treatment area may be flushed with or without aspiration to assist in separating and capturing occlusive material. The flush may be applied through treatment device via a fluid line connected to a flush source. Alternately, flush may be applied from the side arm of the introducer sheath.

In some embodiments, both aspiration and flush may be applied to the treatment site. For example, an aspiration source may be connected to the treatment device and a flush source may be connected to the introducer 103. Conversely, an aspiration source may be connected to the introducer 103 and a flush source may be connected to the treatment device 101. Alternately, both are connected to the treatment device 101, or both are connected to the introducer 103.

During separation and/or removal of obstructive material from a treatment site by the treatment assembly, the distal capture sheath may capture and contain any material that has not been aspirated or otherwise removed by treatment device.

During or after separation and/or removal of obstructive material from a treatment site by the treatment assembly, the treatment device can be removed from the introducer sheath 110 (FIG. 1). Aspiration applied through the introducer sheath 110 can reduce embolic particles during device removal. Inclusion of a funnel on the introducer sheath 110 may also reduce the possibility of embolic particles remaining in the vasculature as the treatment device is removed.

At any point before, during, or after engagement of the cutting elements with the obstructive material, the treatment device and/or treatment assembly can be configured to deliver energy at the treatment site. For example, the treatment device and/or treatment assembly may be configured to vibrate and/or emit ultrasonic energy.

Conclusion

Although many of the embodiments are described above with respect to systems, devices, and methods for retrieving clot material from a blood vessel lumen, the technology is applicable to other applications and/or other approaches, such as removal and/or modification of other structures within any body lumen. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-28B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for modifying and/or removing obstructive material from a lumen of a blood vessel, the system comprising:
- a first elongated member having a proximal portion and a distal portion configured to be intravascularly positioned at a treatment site in the blood vessel adjacent the obstructive material, wherein the first elongated member defines a lumen extending therethrough;
- a second elongated member having a proximal portion and a distal portion configured to be intravascularly positioned at the treatment site, wherein the second elongated member is rotatably disposed within the lumen of the first elongated member; and
- a helical ribbon cutting element configured to cut obstructive material at the treatment site, the helical ribbon cutting element having a proximal end region at the distal portion of the first elongated member, a distal end region at the distal portion of the second elongated member, a sharpened proximal facing longitudinal edge, an atraumatic or blunted distal facing longitudinal edge; and
- an expandable tapered wire mesh with a proximal opening and a closed distal portion, and a cross-sectional dimension therebetween that decreases in a distal direction and configured to be inserted through and out of the lumen of the second elongated member.

2. The system of claim 1, wherein the rotation of the second elongated member relative to the first elongated member causes the helical ribbon cutting element to expand away from a longitudinal axis of the second elongated member.

3. The system of claim 1, wherein the helical ribbon cutting element is wound more than one turn.

4. The system of claim 1, wherein the helical ribbon cutting element comprises a resilient metal alloy.

* * * * *